US 6,404,206 B1

(12) United States Patent
Sperschneider

(10) Patent No.: US 6,404,206 B1
(45) Date of Patent: Jun. 11, 2002

(54) PROCESS AND CIRCUIT FOR TESTING A SOLDER JOINT FOR FAULTS

(75) Inventor: Eckhard Sperschneider, Neubiberg (DE)

(73) Assignee: Macrotron Process Technologies GmbH, Kirchheim (DE)

( * ) Notice: Subject to any disclaimer, the term of this patent is extended or adjusted under 35 U.S.C. 154(b) by 0 days.

(21) Appl. No.: 09/433,954

(22) Filed: Nov. 4, 1999

Related U.S. Application Data

(63) Continuation of application No. PCT/EP98/02615, filed on May 4, 1998.

(30) Foreign Application Priority Data

May 5, 1997 (DE) .......................................... 197 18 940

(51) Int. Cl.[7] .............................................. G01R 31/00
(52) U.S. Cl. ....................... 324/537; 324/158.1; 702/58
(58) Field of Search ................................. 324/500, 537, 324/750, 158.1; 702/57, 58, 82

(56) References Cited

U.S. PATENT DOCUMENTS

| 5,105,149 A | * | 4/1992 | Tokura ........................ 324/752 |
| 5,118,192 A | * | 6/1992 | Chen et al. .................. 356/602 |
| 5,291,535 A | | 3/1994 | Baker et al. .................. 378/22 |
| 5,493,594 A | | 2/1996 | Hamada et al. ............... 378/34 |
| 5,495,424 A | * | 2/1996 | Tokura ........................ 702/82 |
| 6,023,663 A | * | 2/2000 | Kim ............................. 702/81 |

FOREIGN PATENT DOCUMENTS

| EP | 0236001 | 9/1987 |
| EP | 433803 | 6/1991 |
| WO | WO 97/17605 | 5/1997 |

OTHER PUBLICATIONS

Publication No. XP 000179243, Driels, et al. "Automatic Defect Classification of Printed Wiring Board Solder Joints," Jun. 1990, vol. 13, No. 2, pp. 331–340.
Publication No. XP 000143745, Parks, et al., "A Solder Joint Inspection System for Automated Printed Circuit Board Manufacturing," May 1990, vol. 2, pp. 1290–1295.
Publication No. XP 000455263, Feldmann, et al., "Closed Loop Quality Control in Printed Circuit Assembly," Jun. 1994, vol. 17, No. 2, pp. 270–276.

* cited by examiner

Primary Examiner—Safet Metjahic
Assistant Examiner—Wasseem H. Hamdan
(74) Attorney, Agent, or Firm—Crowell & Moring LLP

(57) ABSTRACT

In a process and apparatus for inspecting welding points (or solder joints) for defects by means of X-rays, before the welding points are inspected, the values of predeterminable measurement parameters, such as height of a welding meniscus or rise of a grey scale value curve generated by the device, are determined for reference welding points. When the welding points are subsequently inspected, selected measurement parameters are evaluated.

41 Claims, 21 Drawing Sheets

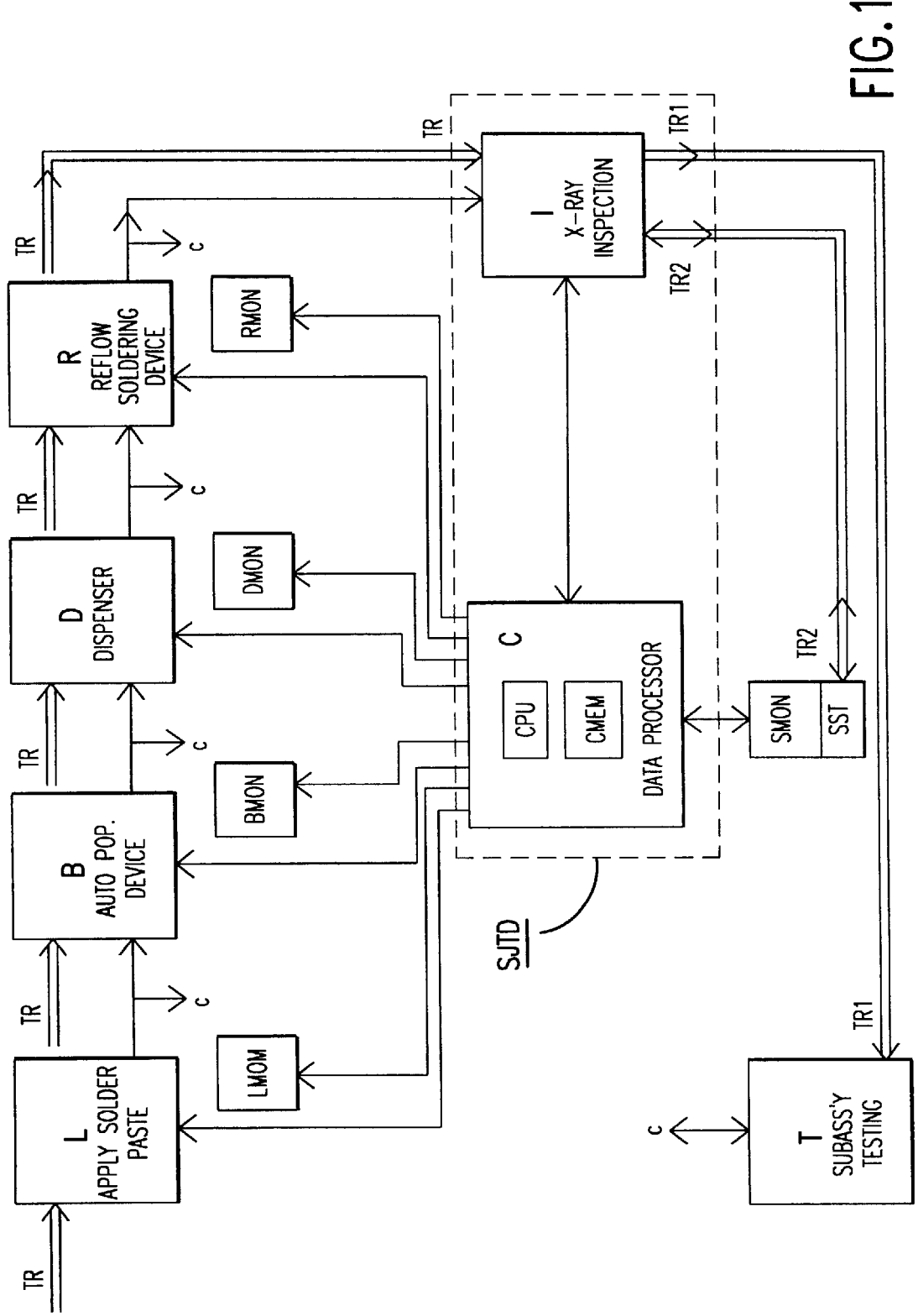

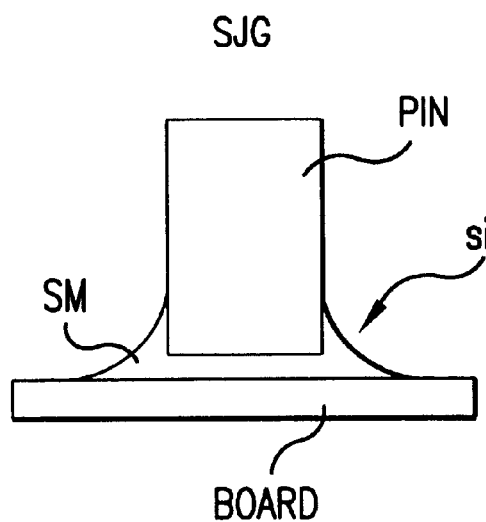
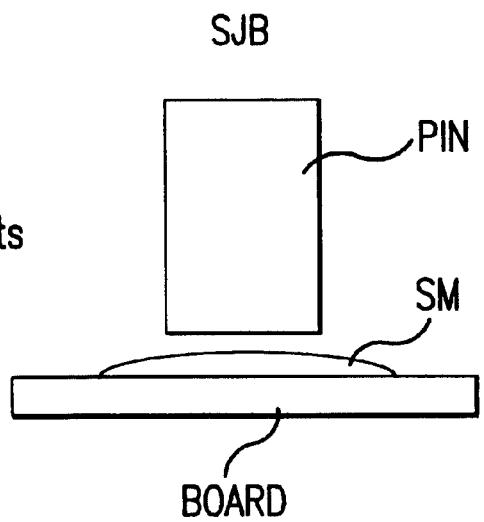
FIG.6a
FIG.6b
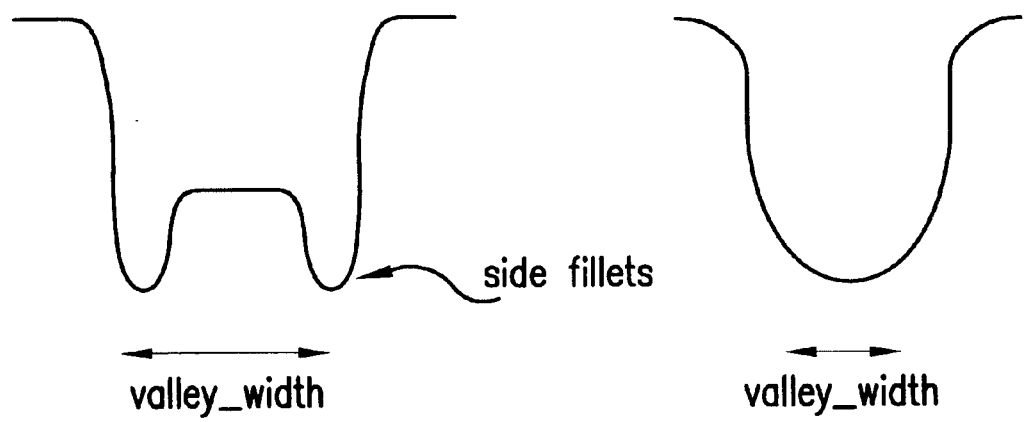
FIG.6c
FIG.6d

SOT

FIDUCIAL

DISCRETE

Jlead

PTH

GULLWING

Sos_2d

Solder Joint Type

| Cumulative | | |
|---|---|---|
| 26% | (240) | TANTC |
| 19% | 181 | TANTA |
| 10% | 100 | 0204R |
| 9% | 91 | SMA |
| 7% | 65 | TANTD |
| 5% | 52 | OFP64 |
| 5% | 48 | TANTC |
| 5% | 48 | 0805C |
| 4% | 39 | XTRL5 |
| 2% | 19 | 0805R |
| 2% | 18 | 0805CF |
| 2% | 16 | 1206C |
| 1% | 23 | 5064P |
| 1% | 7 | 1206R |
| 0% | 1) | 5020NPX |

Solder Joint/Type

| | | | Pin |
|---|---|---|---|
| 24% | (61) | 01_D112 | 1 |
| 16% | 33 | 01_D114 | 2 |
| 10% | 24 | 03_D112 | 4 |
| 5% | 22 | 02_D114 | 2 |
| 5% | 22 | 03_D114 | 2 |
| 5% | 13 | 02_D112 | 2 |
| 4% | 10 | 01_D112 | 1 |
| 3% | 6 | 02_D111 | 2 |
| 3% | 6 | 04_D111 | 2 |
| 3% | 6 | 04_D111 | 1 |
| 2% | 5 | 03_D113 | 2 |
| 2% | 4 | 04_D113 | 2 |
| 1% | 3 | 02_D111 | 3 |
| 2% | 3 | 01_D114 | 2 |
| 1% | 2 | 01_D112 | 2 |
| 0% | 2 | 01_D111 | 1 |
| 0% | 1 | 01_D112 | 1 |
| 0% | 1 | 03_D112 | 2 |
| 0% | 1 | 03_D111 | 2 |
| 0% | 1 | 03_D113 | 2 |

Failure Type

| 2% | (5) | 70 SMD Misplaced |
|---|---|---|

Rule Failure

| 70% | (171) | 24 |
|---|---|---|
| 11% | 28 | 40 |
| 6% | 15 | 4 |
| 4% | 9 | 23 |
| 3% | 8 | 1 |
| 3% | 7 | 16 |
| 2% | 5 | 19 |
| 0% | 2 | 23 |

[Top] [Bottom] [True] [Process] [Pseudo] [Close]

FIG. 16

OPERATING MODE CONFIGURATION

Display
- ◉ Monitor    ◇ Series of Measurements

Subassemblies
500

[ OK ]  [ Abort ]  [ Help ]

FIG.17a

LIMITED VALUE CONFIGURATION

| Measured Value |
| --- |
| ToeBoardDelta |
| FilletSolder |
| MeasureFilletWidth |
| HeelPadDelta |
| PadBoardDelta |

CIS  PTH  SOT  IC

Upper Warning Limit
150

Lower Warning Limit
40

Minimum  35          Maximum  80

[ End ]  [ Accept ]  [ Store ]  [ Reset ]  [ Help ]

FIG.17b

SUBASSEMBLIES INFORMATION

| | | Class | N/A | DIS | PTH | SOT | IC |
|---|---|---|---|---|---|---|---|
| Project | 108015 | | | | | | |
| Memory Allocated | 500000 | Measured Values | 0 | 4 | 0 | 4 | 7 |
| Boards in Memory | 22 | Components | 33 | 34 | 0 | 6 | 11 |
| Memory Per Board | 17824 | Solder Joints | 66 | 70 | 0 | 16 | 268 |

[ OK ]    [ Help ]

FIG.18

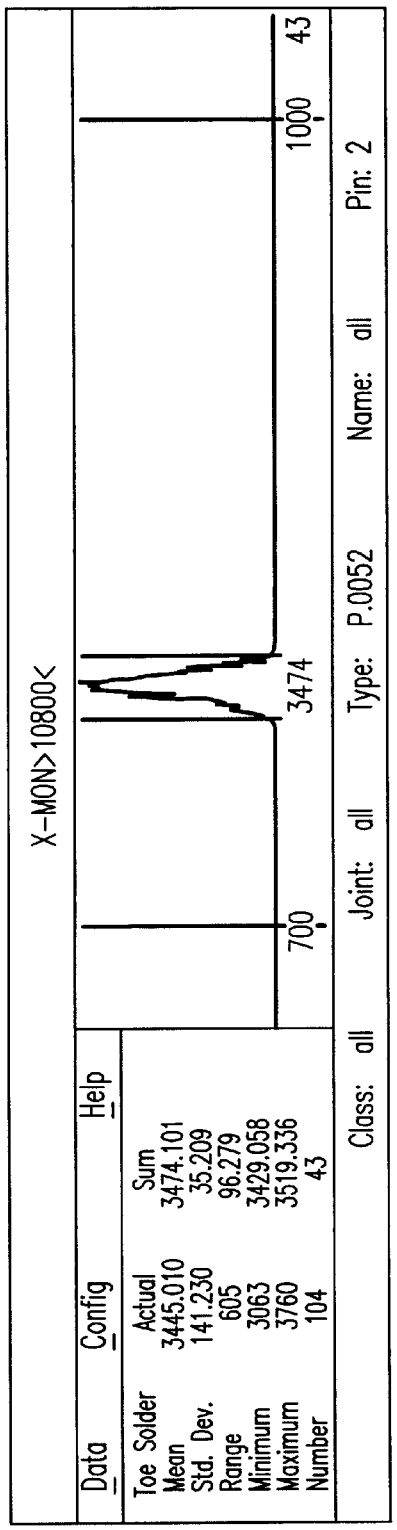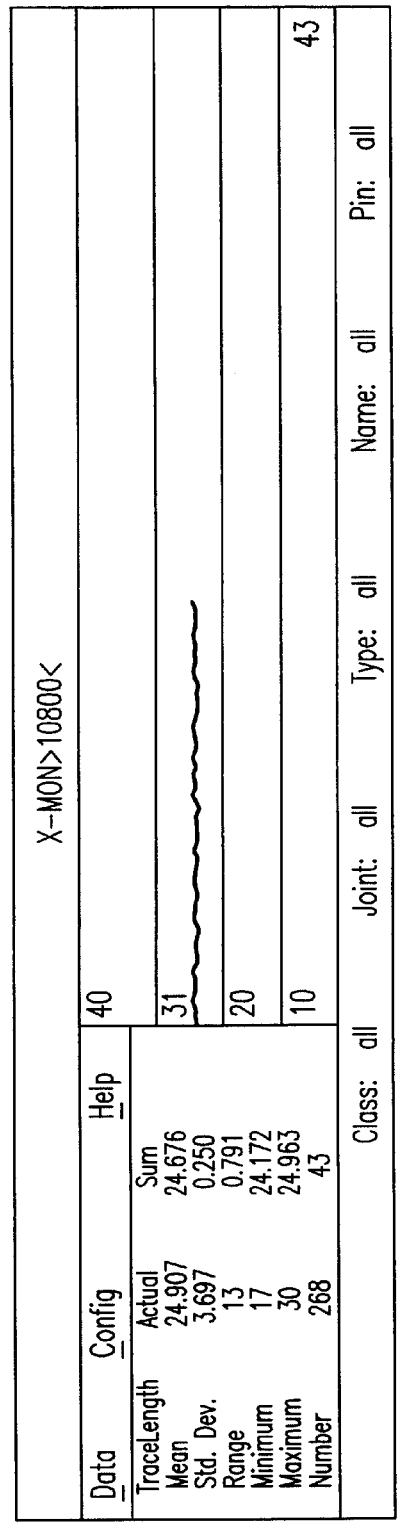
FIG.19a
FIG.19b

PROCESS AND CIRCUIT FOR TESTING A SOLDER JOINT FOR FAULTS

This application is a continuation of co-pending International Patent Application No. PCT/EP98/02615 filed May 4, 1998, designating the United States of America, which is incorporated in its entirety by reference herein.

BACKGROUND OF THE INVENTION

The invention relates to a process and a circuit arrangement for selecting at least one measuring parameter for testing a solder joint to detect faults therein.

The quality of solder joints on printed circuit boards can be checked for defects by means of X-rays. In the process, solder-joint-specific quality information is formed, either the information "solder joint defect-free" or the information "solder joint defective" being formed for each solder joint. This information is printed out with reference to printed circuit boards, this print-out, together with the associated printed circuit board, being supplied to a repair workstation. There, the printed circuit boards which have at least one solder joint for which the information "solder joint defective" was formed is subjected to subsequent treatment, the allegedly defective solder joint being checked visually. If the result is that the solder joint is actually defective, the contact point having the original defective solder joint is re-soldered. A test is then carried out again to see whether this solder joint is now defect-free. These operations are noted in a report, which, if necessary, is available for statistical evaluation.

EP 0 236 001 B1 has already disclosed a process and a device for measuring structural properties of selected regions of a manufactured printed circuit board having solder joints provided thereon. The device has an X-ray device for generating an X-ray beam, an imaging device for registering the X-rays transmitted through the printed circuit board in order to generate a corresponding electronic image, a processing device for converting the electronic image into an image encoded in accordance with a grey scale, and a computing device which carries out measurements on the image that has been encoded in accordance with a grey scale on the basis of measuring algorithms which are selected from a data library and which relate to predefinable electronic standard components and arrangements and to specific types of solder-joint defect that are associated with these (including "solder ball", "excess solder", "cold solder joint"). The computing device also generates an output signal, which corresponds to a change in the measurements of the image encoded in accordance with a grey scale from predetermined measuring standards, which, for their part, correspond to desired structural properties, which are contained in the library.

Testing of solder joints for freedom from faults can be performed in such a way that a user of a testing device effects the measurement of a plurality of reference solder joints by means of X-rays in respect to one or more measuring parameters. These measuring parameters define particular single aspects of the solder joints, for example the longitudinal dimensions of the solder joints, the lateral dimensions of the solder joints, the valley width of a cross-section of a solder joint and a difference in height between vertex points and valley points of the solder joints. The measurement of reference solder joints by means of X-rays generates information designating grey values of the solder joints. Examples for such information are shown in the lower parts of FIGS. 2 to 5. The information generated by the measurement provides reference values for subsequent testing of solder joints. In conventional systems however subsequent testing of solder joints leads to a large extent to results which are objectively wrong: on the one hand solder joints which are evaluated as free of faults are in fact faulty, on the other hand solder joints which are evaluated as faulty are in fact free of faults.

A solder joint inspection system is known from PARK J S ET AL: A SOLDER JOINT INSPECTION SYSTEM FOR AUTOMATED PRINTED CIRCUIT BOARD MANUFACTURING, PROCEEDINGS OF THE INTERNATIONAL CONFERENCE ON ROBOTICS AND AUTOMATION, CINCINNATI, MAY 13–18, 1990, vol. 2, May 13, 1990, pages 1290–1295, XP000143745 INSTITUTE OF ELECTRICAL AND ELECTRONICS ENGINEERS. In the known solder joint system four frames of solder joint images are used and 15 features are extracted from the images to catagorize the most important seven classes of solder joint defects.

SUMMARY OF THE INVENTION

On the basis of this prior art, the object of the invention is to specify a process and a circuit arrangement of the type mentioned at the beginning, which reduces the probability of the occurrence of defective results in the testing of solder joints.

According to the invention, this object is achieved by a process and a circuit arrangement in which measurement information of fault-free reference solder joints of a predefinable type is correlated with measurement information of at least one faulty reference solder joint of the same type. Based on this correlation measuring parameters are selected for testing solder joints of the same type. Measuring parameters are selected which facilitate the detection of a particular type of solder joint fault. The use of the selected measuring parameters leads to test results, which have a high probability of being correct. This on the one hand avoids solder joints which are in fact fault-free being judged incorrectly as faulty, rejected and subjected to a repair which is not in fact necessary. On the other hand it avoids solder joints which actually are faulty being judged fault-free and causing non-function when installed in electronic systems.

In a further advantageous embodiment of the process according to the invention, a solder joint when tested is judged to be fault-fee if the measuring parameter value formed in the test is of at least the same size as a second threshold specific to a measuring parameter which is smaller than a first threshold specific to a measuring parameter by a threshold value deviation specific to a measuring parameter. Thereby the amount of solder joints which would otherwise be judged faulty but which are in fact fault-free and would correspondingly be judged fault-free is increased.

In yet a further advantageous embodiment of the process according to the invention, the solder joint is tested for the extent of a contact area formed between the solder material and contact element. The extent of the contact area formed between the solder material and contact element is compared with a predefinable contact-area reference value and the solder joint is judged to be a fault-free solder joint or to be a faulty solder joint as a function of the result of the comparison.

This embodiment of the process according to the invention can be carried out using relatively little data processing capacity and with a relatively small number of measurements of reference solder joints since this embodiment of the process according to the invention requires only a few measuring parameters. It merely requires at least a first measuring parameter by means of which a piece of information is generated which indicates a probability of, e.g., at least 50% for the existence of a galvanic contact between solder material and contact element as well as second measuring parameters by means of which a piece of information is generated which defines the magnitude of the contact area. For example the extent of the contact area can be determined precisely enough by means of a measuring parameter, which designates the longitudinal extent of the solder joint, and by means of a further measuring parameter, which designates the lateral extent of the solder joint.

Other objects, advantages and novel features of the present invention will become apparent from the following detailed description of the invention when considered in conjunction with the accompanying drawings.

BRIEF DESCRIPTION OF THE DRAWINGS

FIG. 1 shows an arrangement of devices in connection with carrying out the process according to the invention;

FIGS. 14, 15 and 16 show monitor displays, formed within the context of the process according to the invention, of faults as a statistical evaluation;

FIGS. 17a, 17b and 18 show monitor displays, formed within the context of the process according to the invention, in connection with the configuration of measurements, and respectively, reference values;

DETAILED DESCRIPTION OF THE DRAWINGS

Figure 2A:
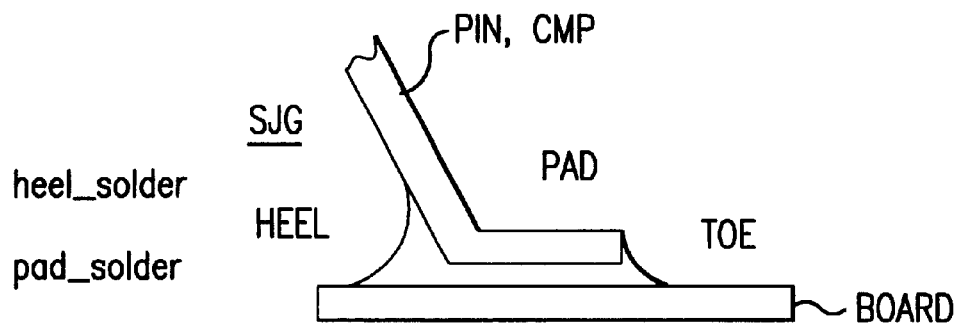
FIG. 2 shows a section view, a grey value image and a graphical illustration of an electrical signal of the grey-value image of a first type of solder joint (SOT solder joint)

The arrangement illustrated in FIG. 1 comprises the circuit arrangement SJTD for testing of solder joints according to the invention. For example the circuit arrangement consists of a data processing device C and an X-ray inspection device I. The data processing device C and the X-ray inspection device I serve to carry out the inventive process of testing solder joints for freedom from faults.

Furthermore the data processing device C and the X-ray inspection device I can also carry out further measurement and control procedures, for example in connection with the production of solder joints as illustrated in FIG. 1. The arrangement illustrated in FIG. 1 consists of a first device L, which applies solder paste to printed circuit board blanks, a so-called dispensing device D, a second device B, which is formed by an automatic population device and populates the printed circuit boards, preferably using the SMD technique, with one or more components or subassemblies, a third device R, which is formed by a reflow soldering device, an X-ray inspection device I, a data processing device C, a repair workstation SST, which is also equipped for the verification of defect-free printed circuit boards (monitor SMON, which displays data generated by C) and has a keyboard (not illustrated) for controlling the monitor display or for carrying out dialogue with the data processing device C, as well as a device T which carries out electrical subassembly tests.

The devices L, D, B, R, I and T are in themselves devices which are known. The device L is, for example, a product from the MPM company bearing the product description Ultraprint; the device D is, for example, a product from the 3000 series from the Cama/lot company; the device B is, for example, an SMD automatic population device from the Siemens, Quad, Fuji or Panasonic MPM companies; the device R is, for example, a furnace from the BTU company or an appropriate product from the Elektrovert company; the device I is, for example, a product from the NICOLET (NIS) company bearing the product description CX13000/5000 and MV6000, and the device T is, for example, a product from the Hewlett Packard company bearing the product description HP 3070.

The devices L, B, D, R, and the repair workstation SST have assigned to them screen monitors LMON, BMON, DMON, RMON and SMON, which are connected to the data processing device C.

The data processing device C has assigned to it a control program defining the process according to the invention. It is indicated schematically in FIG. 1 with its controller CPU and with a memory CMEM which, inter alia, serves for the acceptance of the information which is formed within the context of the process according to the invention and to which access is made in order to form this information.

For the fabrication of solder joints and for the control or regulation of the corresponding fabrication process the data processing device C is connected to the devices L, D, B, R, I and T. The data processing device C receives from these devices first data which relate to the printed circuit boards or solder joints treated in these devices, and/or second data which relate to the devices themselves. The first and/or second data can also be supplied by a device (e.g. L) to the device (e.g. B) that is in each case arranged next in line. The data processing device C supplies the devices L, B, D and R with control or regulation information, which is formed as a function of solder-joint-specific quality information and/or the solder-joint-specific measurement information.

The monitors LMON, BMON, DMON, RMON and SMON are supplied by the data processing device C with, inter alia, solder-joint-specific quality information, solder-joint-specific measurement information and, where appropriate, statistical information about the frequency of the occurrence of defects. This information is displayed on the monitors. Monitor displays of this type are illustrated in FIGS. 8, 14 to 16 and 19.

The transport route of the printed circuit boards is designated TR in FIG. 1. From the output of the X-ray inspection device I, a first transport path TRI leads to the device T; transported on this transport path are printed circuit boards which have been detected as defect-free by the X-ray inspection device I or by the data processing device C. However, provision may also be made for printed circuit boards detected as defect-free to be supplied to the repair station SST for the purpose of verifying the freedom from defects.

In addition, a second transport route TR2 leads from the outlet of the X-ray inspection device I to the repair workstation SST; this transport path transports printed circuit boards which are detected as defective by the X-ray inspection device I or by the data processing device C. Following the repair, the printed circuit boards can be transported back on the transport path TR2 from the repair workstation SST to the X-ray inspection device I, where they are once more subjected to an inspection.

The X-ray inspection device I is capable, in a manner known of itself, of forming solder-joint-specific information, either the information "solder joint defect-free" or the information "solder joint defective" being formed for each solder joint. Alternately it is provided that the X-ray inspection device I which is controlled by the data processing device C measures reference solder joints and further solder joints corresponding to the process according to the invention, whereby the data processing device C evaluates the measurements formed ("measuring parameter values").

By means of the process according to the invention solder joints (SJG, SJB in FIGS. 2 to 6) are tested for freedom from faults by means of X-rays, whereby the solder joints can be arranged on a substrate, preferably on a circuit board (BOARD, FIGS. 2 to 6).

Figure 2B:
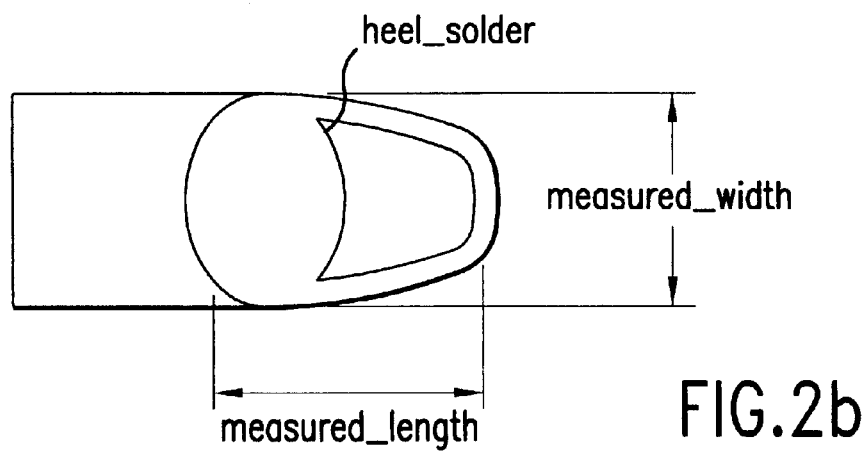
Figure 2C:
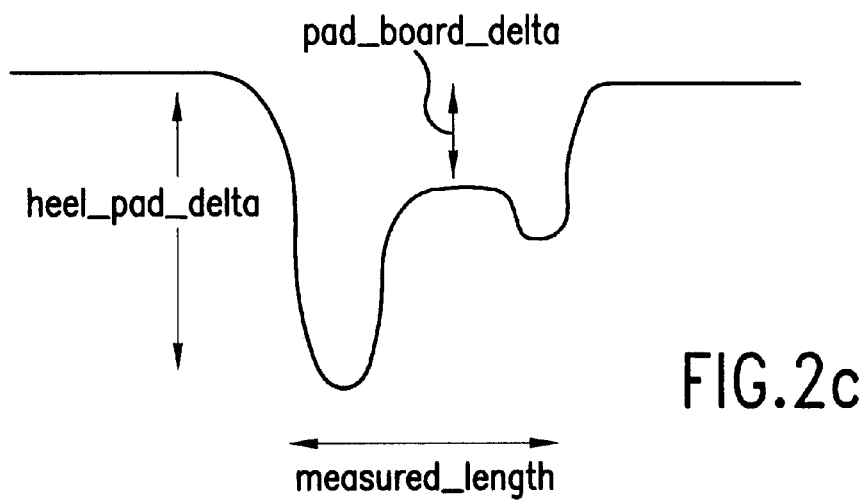
Figure 3A:
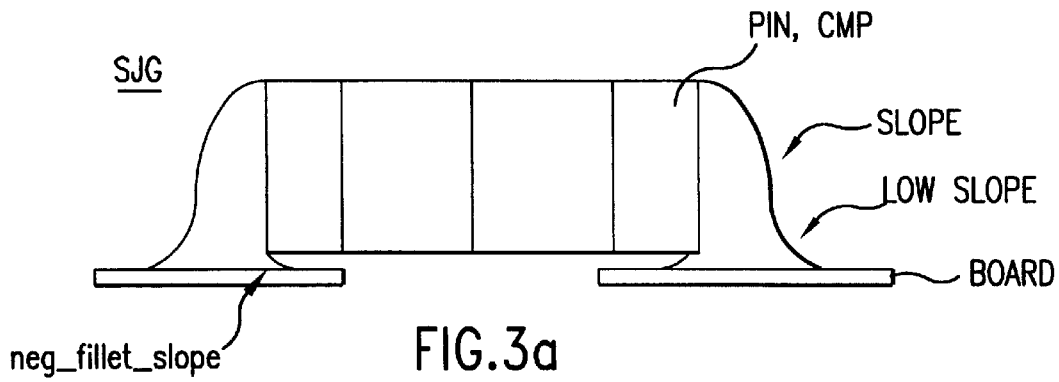
FIG. 3 shows a section view, a grey-value image and a graphical illustration of an electrical signal of the grey-value image of a second type of solder joint (solder joint for discrete components)
Figure 3B:
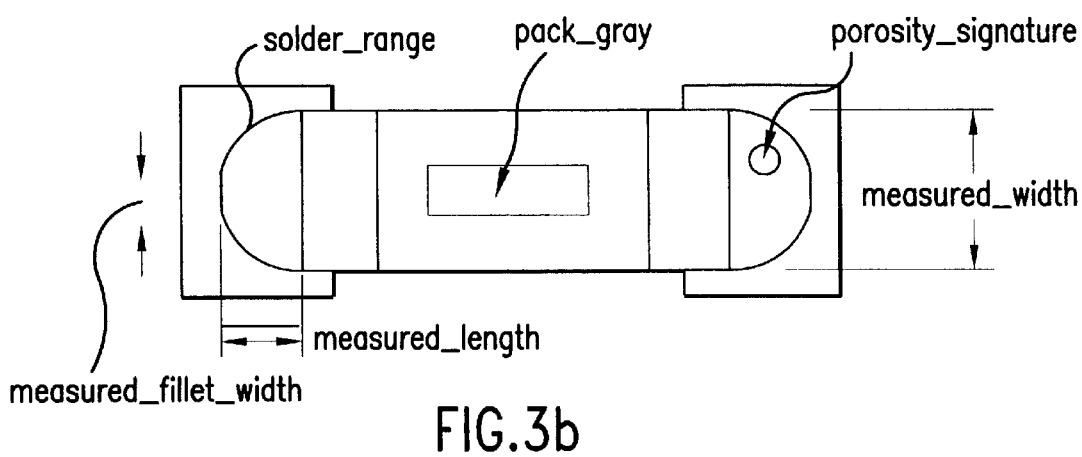
Figure 3C:
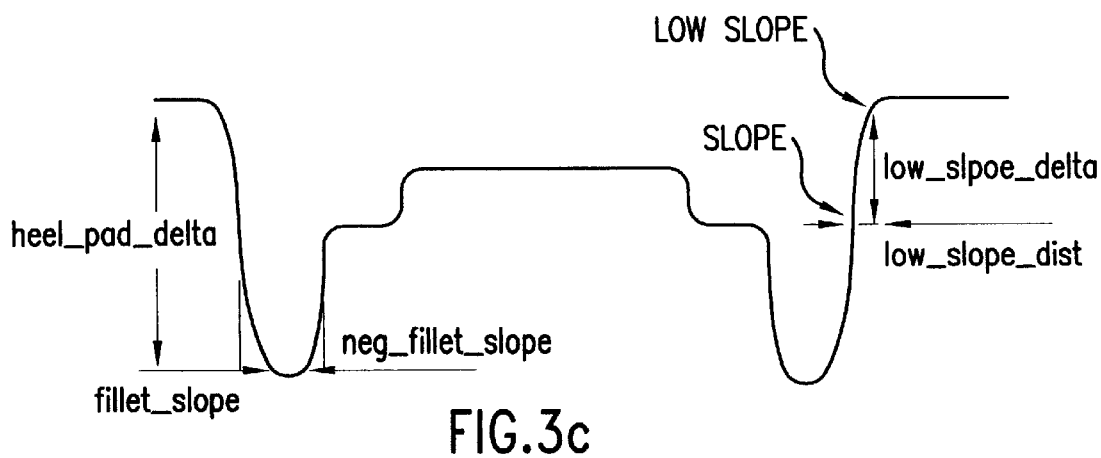
Figure 4A:
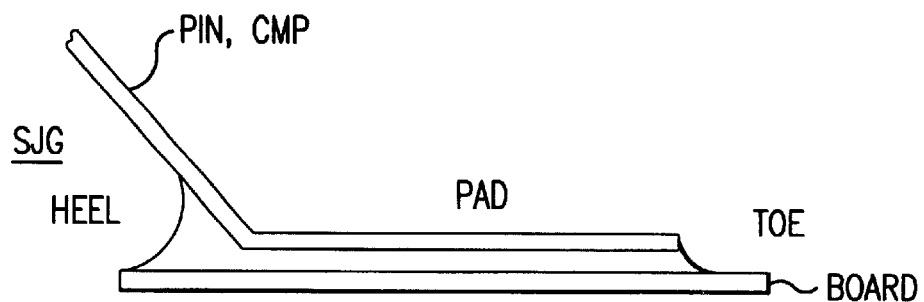
FIG. 4 shows a section view, a grey-value image and a graphical illustration of an electrical signal of the grey-value image of a third type of solder joint (gull-wing pin solder joint)
Figure 4B:
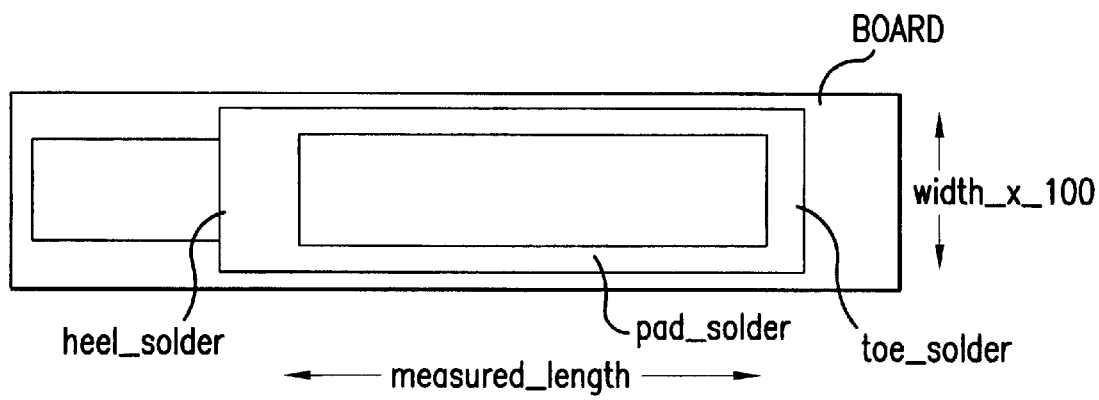
Figure 4C:
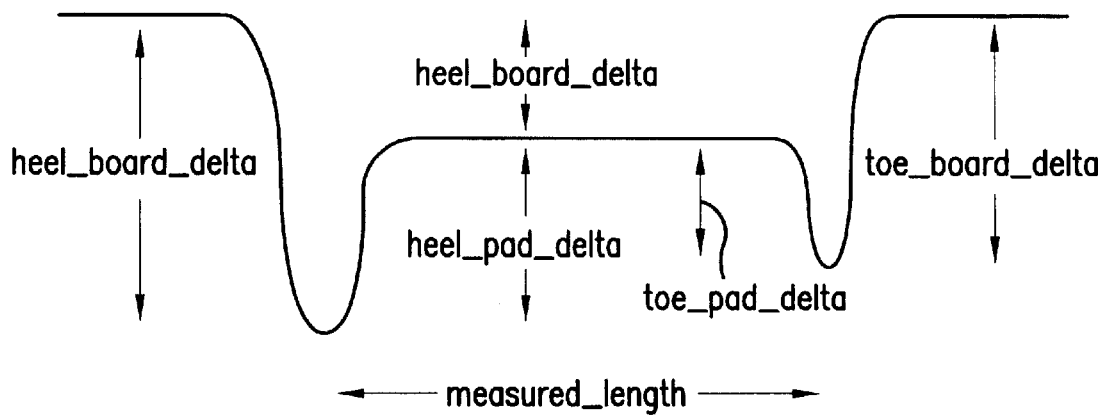
Figure 5A:
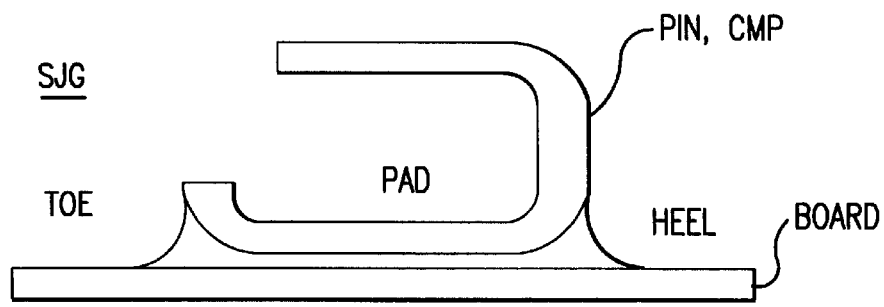
FIG. 5 shows a section view, a grey-value image and a graphical illustration of an electrical signal of the grey-value image of a fourth type of solder joint (solder joint for J-shaped contact elements "J-Lead Pins")
Figure 5B:
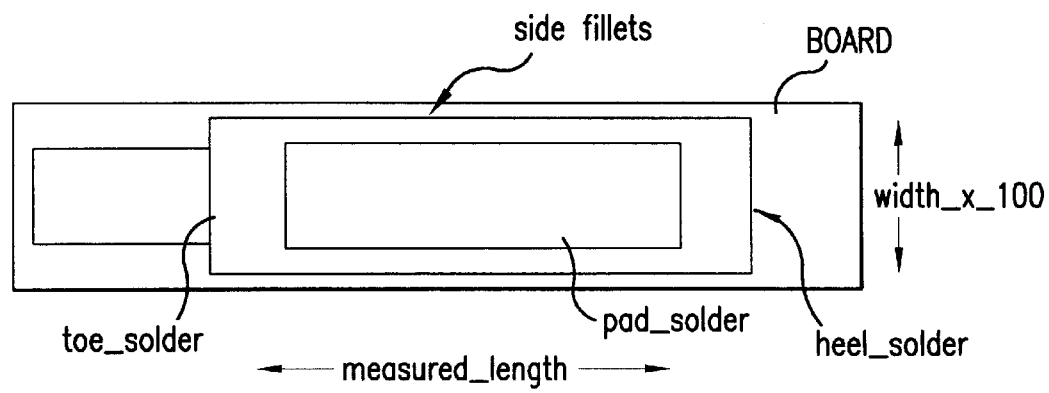
Figure 5C:
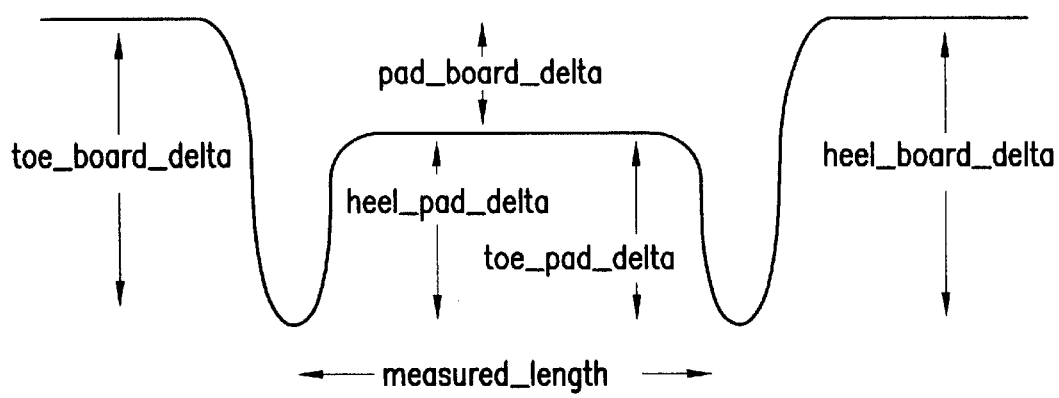

As illustrated in FIGS. 2 to 6 a fault-free solder joint SJG has solder material SM, whereby the solder material SM of a fault-free solder joint SJG is electrically connected to a contact element PIN of a component CMP (for example FIG. 3: discrete component such as capacitor, resistor; integrated circuit IC). The solder joints SJ are assigned to a predefinable solder-joint type as a function of the shape of the contact element PIN in the region of the solder joint SJ. For example the solder joint illustrated in FIG. 2 is a so called SOT ("Small Outline Transistor") solder joint; the solder joint illustrated in FIG. 3 is a solder joint for discrete components, the solder joint illustrated in FIG. 4 is a gull wing pin solder joint and the solder joint illustrated in FIG. 5 is a solder joint for J-shaped contact elements, ("J-Lead Pin solder joint", e.g.: Small Outline J-lead SOJ). In the context of the process according to the invention solder joints of all types can be tested. Examples thereof are illustrated in FIGS. 6b and 6c, which are described below.

Figure 6E:
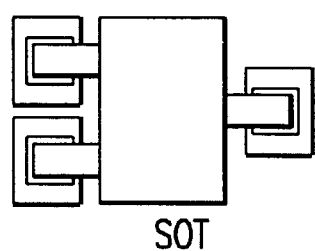
FIGS. 6a–6c show comparison of a fault-free solder joint SJG and of a faulty solder joint SJB as well as several fault-free solder joints of different types.
Figure 6F:
Figure 6G:
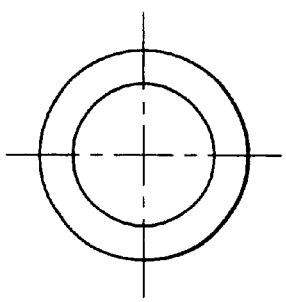
Figure 6H:
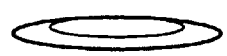
Figure 6I:
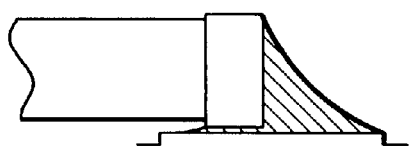
Figure 6J:
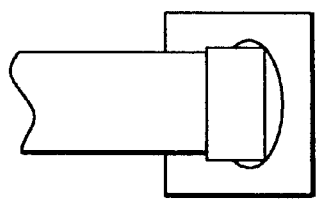
Figure 6K:
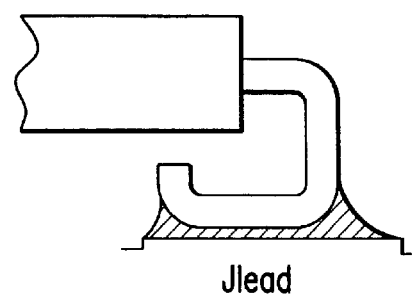
Figure 6L:
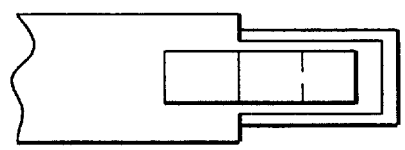
Figure 6M:
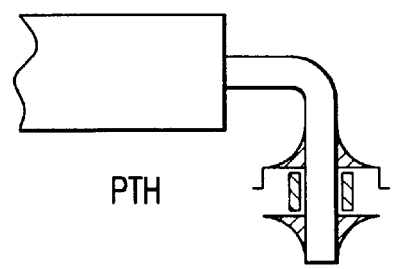
Figure 6N:
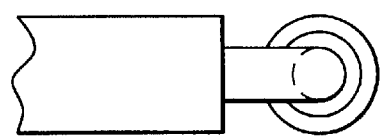
Figure 6O:
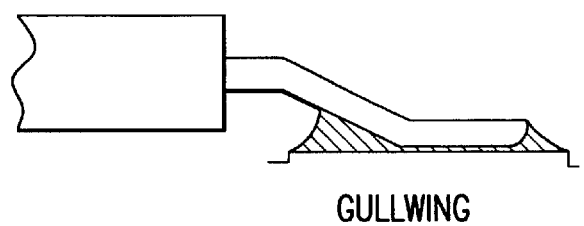
Figure 6P:
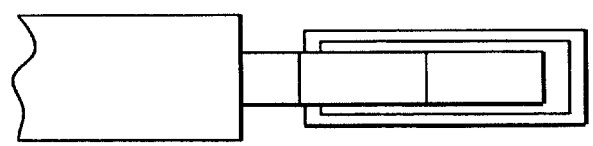

FIG. 6a shows a comparison of a fault-free solder joint SJG with a faulty solder joint SJB. In the upper part of FIG. 6a a section of each of the respective solder joints is illustrated, while in the lower part of FIG. 6a the course of each output signal formed by the X-ray inspection device is illustrated. In the case of the fault-free solder joint SJG (left hand side in FIG. 6a) the soldering material SM forms so called side fillets (lateral menisci or parts of the soldering material which are connected with the contact element PIN); soldering material SM and contact material PIN are connected galvanically to each other and have a common contact area CTA. In contrast to this, in the case of the faulty solder joint SJB (right hand side in FIG. 6a) the soldering material SM does not form side fillets; soldering material SM and contact material PIN are not connected galvanically to each other and do not have a common contact area CTA.

Further arrangements of fault-free solder joints SJG of different solder joint types are illustrated in FIGS. 2 to 5 as well as in FIGS. 6b and 6c. In each of the upper parts of FIGS. 2 to 5 a section of the respective solder joint is illustrated, in each of the center parts of FIGS. 2 to 5 an X-ray image of the respective solder joint is illustrated, while in each of the lower parts of FIGS. 2 to 5 the image of one of the output signals formed by the X-ray inspection device is illustrated. FIG. 6b shows a plan view upon and a section through an SOT (Small Outline Transistor) solder joint, a so-called Fiducial (marker) solder joint and a solder joint for contacting discrete components. FIG. 6c shows a plan view upon and a section through a J-lead solder joint, a so called PTH (Plated Through-hole; solder joint on a through-hole of a circuit board) and a Gull-wing solder joint.

In FIGS. 2 to 5 the reference signs and the terms designate the following:
heel=heel of a solder joint; pad=area of the solder joint (on the circuit board); toe=toe of a solder joint; BOARD=substrate or circuit board; heel solder=quantity of the solder at the "heel"; pad solder=quantity of the solder at the area (here especially in the center region of the solder joint); toe solder=quantity of the solder at the "toe", measured length =measured length of the soldered area; measured width= measured width of the soldered area; slope=rise at the solder meniscus (of the grey-value curve).

Further reference signs and terms used in FIGS. 2 to 5 are given in the table at the end of the description (APPENDIX B).

Figure 7A:
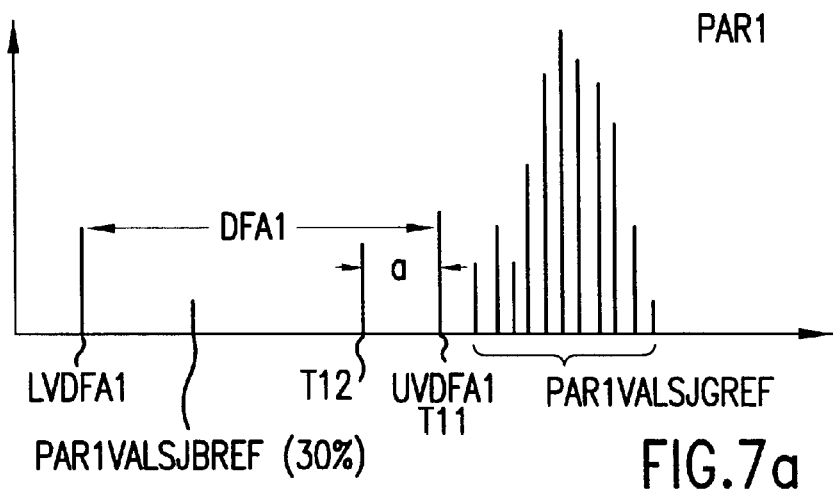
FIG. 7 shows a schematic illustration of measuring parameter values of reference solder joints, fault actual-value ranges, thresholds and threshold deviations which are generated in the context of the process according to the invention.
Figure 7B:
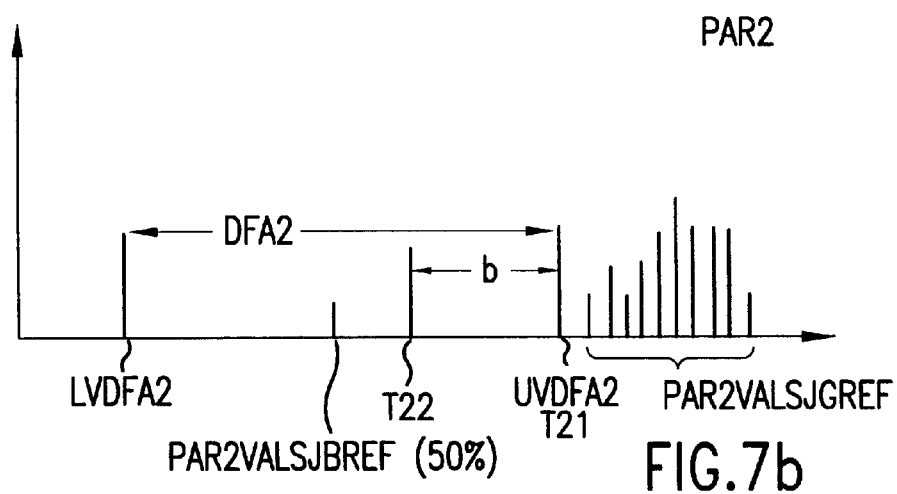
Figure 7C:
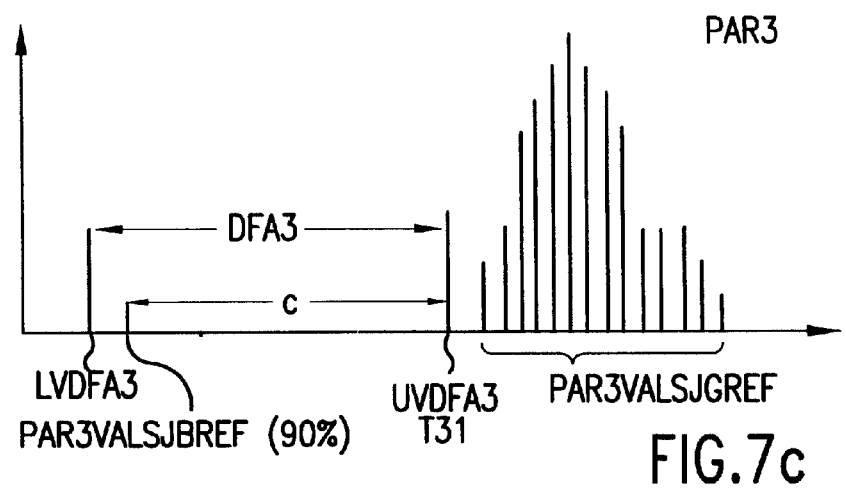
Figure 8:
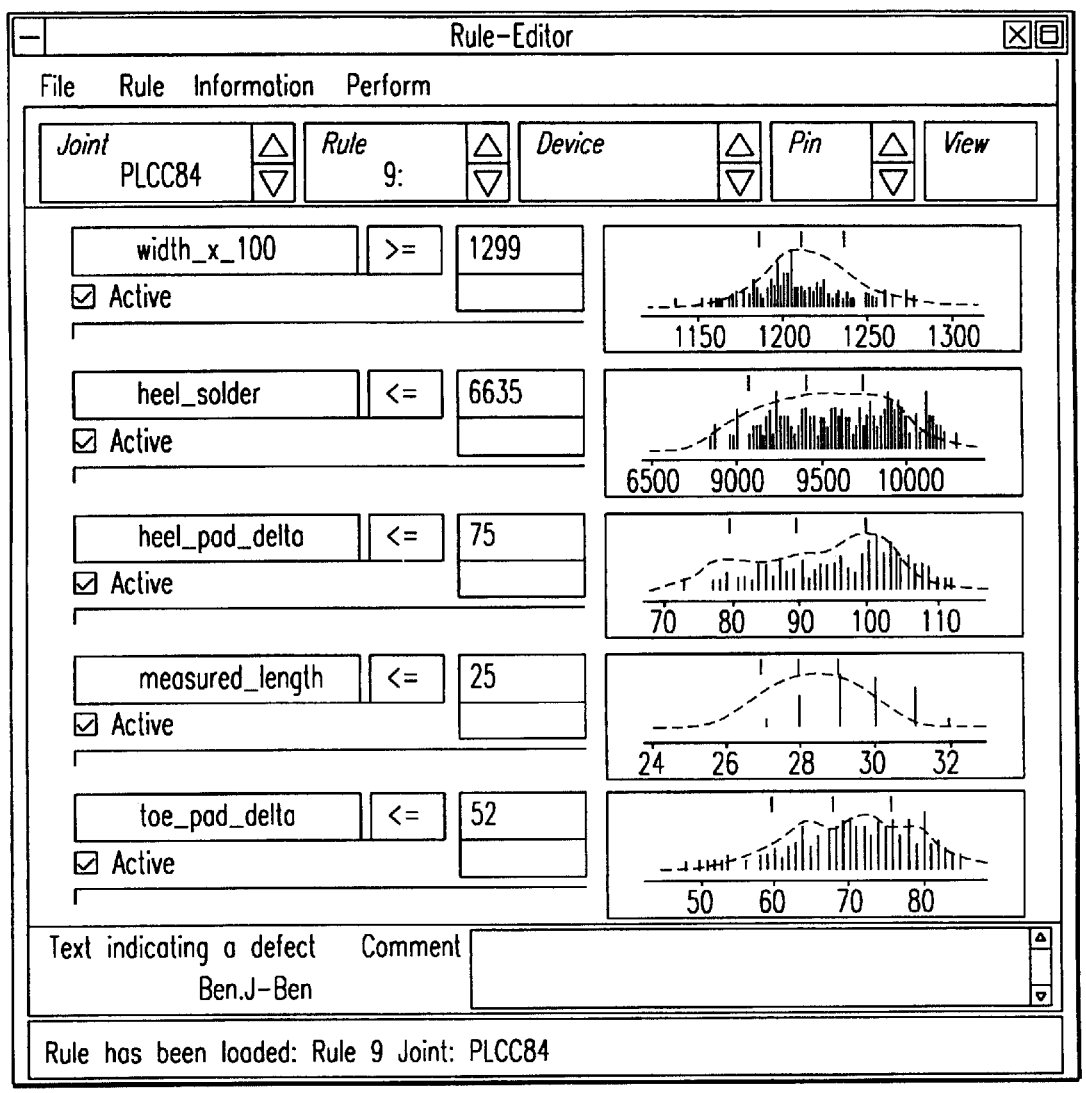
FIG. 8 shows a monitor display of measuring parameter values of different measuring parameters which are defined in the context of the process for measuring solder joints according to the invention.
Figure 9:
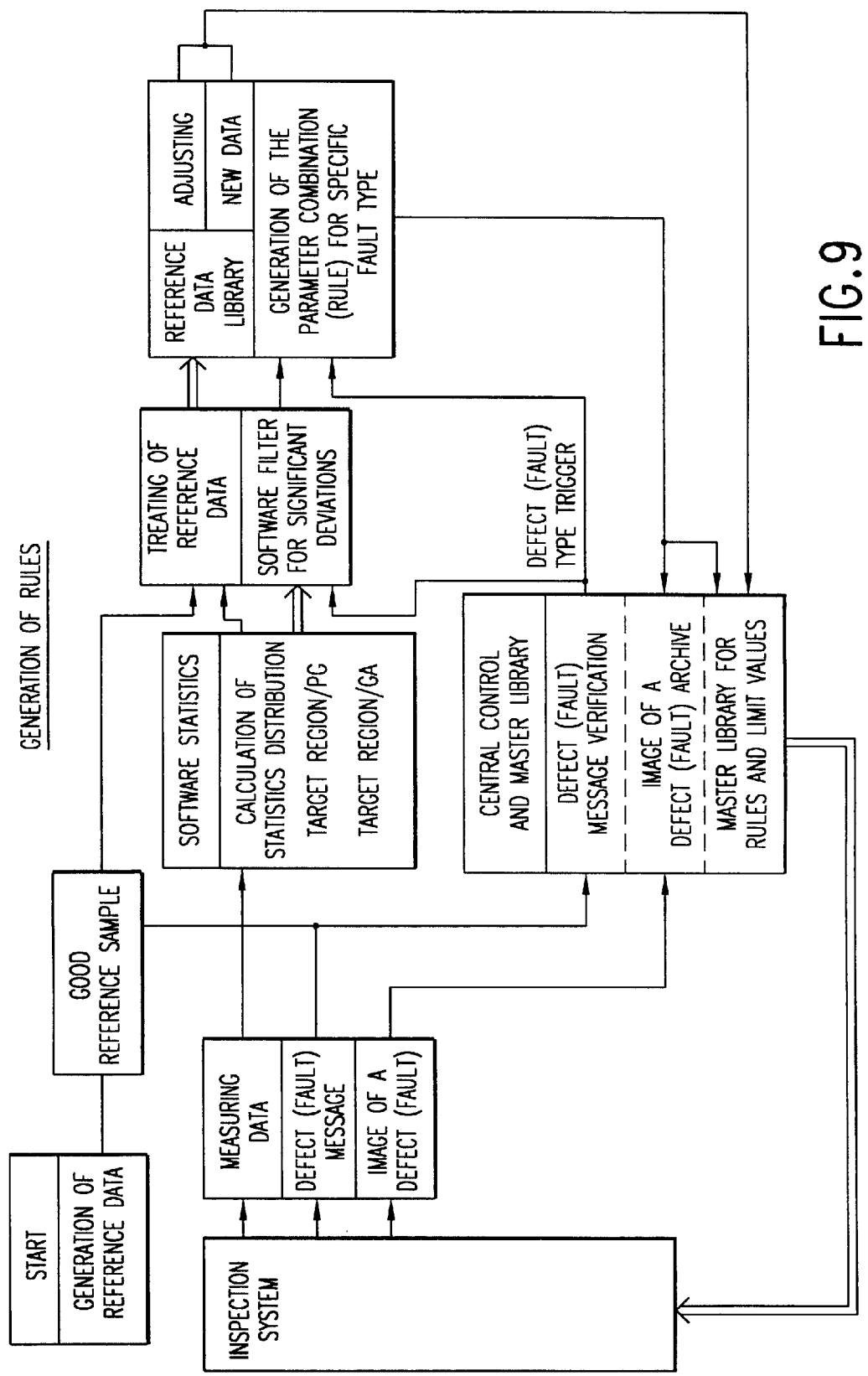
FIG. 9 shows a flow diagram of a cycle in connection with the process according to the invention.

A preferred embodiment of the process according to the invention with which rules for the selection of measuring parameters are generated comprises the following steps:

Before the solder joint SJ is tested, a first number m is determined from measuring parameters (PARi, i=1 . . . m, in FIG. 7: PAR1, PAR2, PAR3), in particular grey-value measuring parameters, in each case a lower range limiting value LVDFAi (FIG. 7) and/or an upper range limiting value UVDFAi of a fault actual-value range DFAi specific to a measuring parameter, whereby a comparatively large fault in the solder joint SJ or a comparatively small fault in the solder joint SJ corresponds to the lower range limiting value LVDFAi, depending on whether the fault-actual value range DFAi lies to the left of the permissible range (range of measuring parameter values of fault-free reference solder joints) as shown in FIG. 7 or in FIG. 8, $2^{nd}$ to $5^{th}$ diagrams, or whether the fault-actual value range DFAi lies to the right of the permissible range as shown in FIG. 8, $1^{st}$ (top) diagram, as will be described below.

A comparatively small fault in the solder joint SJ (FIG. 7 or FIG. 8, $2^{nd}$ to $5^{th}$ diagram) or a comparatively large fault in the solder joint SJ (FIG. 8, $1^{st}$ diagram) corresponds to the upper range limiting value UVDFAi. The measuring parameters PARi in each case describe the topography (geometrical dimensions) of a second number n of fault-free reference solder joints (SJGREFj, j=1. . . n) and/or the internal structure of the n fault-free reference solder joints (SJGREFj) (for example air inclusions (bubbles), cracks), so that m lower range limiting values LVDFAi and/or m upper range limiting values UVDFAi of fault actual-value ranges DFAi specific to a measuring parameter are determined.

Furthermore, before the solder joint SJ is tested, for the first number m of measuring parameters PARi, in each case a measuring parameter value PARiVALSJBREF specific to a reference solder joint, in particular a grey-value measuring parameter, is ascertained from at least one faulty reference solder joint SJBREF of an identical type, so that at least m measuring parameter values PARiVALSJBREF specific to reference solder joints are ascertained for the m measuring parameters PARi of at least one faulty reference solder joint SJBREF of an identical type.

Finally, before the solder joint SJ is tested, the mathematical relationship, in particular its difference from or proportion to the lower range limiting value LVDFAi and/or to the upper range limiting value UVDFAi of the fault actual-value range DFAi specific to a measuring parameter is ascertained for each of the m measuring parameter values PARiVALSJBREF, specific to a reference solder joint, of the identical-type faulty reference solder joints SJBREF.

During the actual testing of the solder joint SJ, a measuring parameter value PAR1VALSJ, in particular a grey-value measuring parameter value, of at least one first measuring parameter PAR1 is ascertained, for which the measuring parameter value PAR1VALSJBREF, specific to a reference solder joint, of at least one faulty reference solder joint SJBREF is arranged closest to (FIG. 7 or FIG. 8, $2^{nd}$ to $5^{th}$ diagrams) or furthest from (FIG. 8, top diagram) the lower range limiting value LVDFA1 of the fault actual-value range DFA1 specific to a measuring parameter, in comparison with other fault actual-value ranges (DFA2, . . . , DFAm) specific to a measuring parameter, and/or for which the measuring parameter value PAR1VALSJBREF, specific to a reference solder joint, of at least one faulty reference solder joint SJBREF is arranged furthest from (FIG. 7 or FIG. 8, $2^{nd}$ to $5^{th}$ diagrams) or closest to (FIG. 8, top diagram) the upper range limiting value UVDFA1 of the fault actual-value range DFA1 specific to a measuring parameter, as compared with other fault actual-value ranges (DFA2, . . . , DFAm) specific to a measuring parameter. As a result the above-mentioned measuring parameter PAR1 (in FIG. 7: "PAR3") is selected for the testing of the solder joint SJ or for the detection/filtering of a particular fault or defect type as will be described below using FIGS. 7 and 8.

In the following description it is assumed that the fault actual-value range is situated on the "left hand side" in respect of the permissible range of the measuring parameter values of fault-free reference solder joints as shown in FIGS. 7 and 8. The invention however also refers to embodiments where the fault actual-value range is situated on the "right hand side" in respect of the permissible range of the measuring parameter values of fault-free reference solder joints, as shown in FIG. 8, diagrams 2–5.

During the testing of the solder joint SJ, at least a second measuring parameter value PAR2VALSJ of a second measuring parameter PAR2 can be ascertained. Preferentially, measuring parameter values of several measuring parameters (e.g.: five) are ascertained in order to increase the probability of obtaining correct information, i.e. "fault-free solder joint" (solder joint defect free) or "faulty solder joint" (solder joint defective).

For the above-mentioned second measuring parameter PAR2 (FIG. 7) the measuring parameter value PAR2VALSJ specific to a reference solder joint, of at least one faulty reference solder joint SJBREF is arranged second closest (FIG. 7 or FIG. 8, diagrams 2–5) to the lower range limiting value LVDFA2 of the fault actual-value range DFA2 specific to a measuring parameter, in comparison with other fault actual-value ranges (DFA3, . . . ) specific to a measuring parameter. In addition or as an alternative thereto, for this second measuring parameter PAR2 the measuring parameter value PAR2VALSJ specific to a reference solder joint of at least one faulty reference solder joint SJBREF is arranged second furthest from the upper range limiting value UVDFA2 of the fault actual-value range DFA2 specific to a measuring parameter, in comparison with other fault actual-value ranges (DFA3, . . . , DFAm) specific to a measuring parameter. In this way the above-mentioned measuring parameter PAR2 is selected for the testing of the solder joint SJ as will be described using FIGS. 7 and 8.

It can be provided that during testing the solder joint, further measuring parameter values of several measuring parameters are ascertained. For example, measuring parameter values of five measuring parameters can be ascertained during the test of the solder joint.

In the above-mentioned process step, before the solder joint SJ is tested, instead of only one identical-type faulty reference solder joint (in FIG. 7: PAR1VALSJBREF or PAR2VALSJBREF) measuring parameter values (PARoVALSJBREF) specific to a reference solder joint of the first number m of measuring parameters PARi can be ascertained from a third number o of faulty reference solder joints (SJBREFP, p=1 . . . o). In this embodiment of the process according to the invention, before the solder joint SJ is tested, at least one measuring parameter value PARiVALAVESJBREF of the faulty reference solder joints SJBREF is derived from each of the o measuring parameter values PARoVALSJBREF, specific to a reference solder joint, of each measuring parameter PARi in accordance with a predefinable algorithm AL1.

In this case, before the solder joint (SJ) is tested, instead of the mathematical relationship of the measuring parameter values PARiVALSJBREF, specific to a reference solder joint, of the faulty reference solder joints SJBREF of an identical type to the lower range limiting value LVDFAi and/or the upper range limiting value UVDFAi of the respective fault actual-value range DFAi specific to a measuring parameter being determined, the mathematical relationship (association) of the derived measuring parameter values PARiVALAVESJBREF, in particular its difference from or proportion to the lower range limiting value LVDFAi and/or to the upper range limiting value UVDFAi of the respective fault actual-value range DFAi specific to a measuring parameter is determined.

In this embodiment of the process according to the invention, during the testing of the solder joint SJ, instead of the measuring parameter value PARLVALSJ, a further measuring parameter value PARi'VALSJ of at least one other first measuring parameter PARi' is ascertained, for which the derived measuring parameter value PARiVALAVESJBREF of the third number o of the faulty reference solder joints is arranged closest to or furthest from the lower range limiting value LVDFAi of the fault actual-value range DFAi, as compared with other fault actual-value ranges (DFA3, . . . DFAm) specific to a measuring parameter, and/or for which the derived measuring parameter value PARiVALA-VESJBREF of the third number o of faulty reference solder joints is arranged furthest from or closest to the upper range limiting value UVDFAi of the fault actual-value range DFAi, as compared with other fault actual-value ranges (DFA3, . . . , DFAm) specific to a measuring parameter.

The above-mentioned predefinable algorithm AL1 is in particular an algorithm by means of which the arithmetic mean value is formed. However the invention is not restricted to this.

The lower range limiting value LVDFAi or the upper range limiting value (FIG. 8, top diagram) of the fault actual-value range DFAi specific to a measuring parameter is determined as a function of a measuring parameter value for which the faulty solder joint has an insufficient contact area between solder material and contact element (PIN), in particular with regard to the physical limiting value.

The upper range limiting value UVDFAi of the fault actual-value range DFAi specific to a measuring parameter or the lower range limiting value LVDFAi (FIG. 8, top diagram) is determined preferably as a function of the distribution function of measuring parameter values of the fault-free reference solder joints SJGREF.

The distribution function of the fault-free reference solder joints is in particular a standard distribution. In this case the upper range limiting value UVDFAi of the fault actual-value range DFAi specific to a measuring parameter is preferably determined as a function of the standard deviation (s).

The upper range limiting value UVDFAi of the fault actual-value range DFAi specific to a measuring parameter (FIG. 7 and FIG. 8, $2^{nd}$ to $5^{th}$ diagrams) is fixed in particular to a value which is slightly smaller or greater than the measuring parameter value of a still fault-free reference solder joint SFGREF.

The solder joint SJ is judged to be fault-free during the testing if the measuring parameter value is at least as large as a predefinable, first threshold value Ti1(in FIG. 7: T11, T21, T31) specific to a measuring parameter.

In particular the first threshold value Ti1 specific to a measuring parameter is of the same size as the upper range limiting value UVDFAi of the fault actual-value range DFAi specific to a measuring parameter.

It can also be provided that the solder joint SJ is judged to be fault-free during the testing if the measuring parameter value is at least as large as a predefinable, second threshold value Ti2 (in FIG. 7: T12, T22, T32) specific to a measuring parameter, which threshold value is smaller or greater, than the first threshold value Ti1 specific to a measuring parameter by a threshold value deviation ia (in FIG. 7: a, b, c) specific to a measuring parameter.

The magnitude of a permissible threshold value deviation a, specific to a measuring parameter, of a first measuring parameter, and/or the magnitudes of further permissible threshold value deviations (b, c), specific to a measuring parameter, of further measuring parameters is determined as a function of a predefinable reference value CTAREF of a contact area CTA, which is formed between the solder material SM and contact element PIN of a solder joint (SJ) to be tested.

The magnitude of a permissible threshold value deviation (a), specific to a measuring parameter, of a first measuring parameter, and/or the magnitudes of further permissible threshold value deviations (b, c), specific to a measuring parameter, of further measuring parameters can also be determined as a function of a predefinable reference value CTAREF of a mathematical combination of the threshold value deviations (a, b, c), in particular the formation of a product, the formation of an average and/or the formation of a sum of the threshold value deviations.

Furthermore the threshold value deviations can also be set as a function of a predefinable degree of quality of the contact area between solder material and contact element. For example the degree of quality will be set relatively high for products having high security requirements, while the degree of quality can be set relatively low for, e.g., electronic products for the entertainment industry.

As a function of measuring parameter values of first measuring parameters a piece of information is generated which designates a probability (in particular greater than 50%) for the existence of a galvanic contact between solder material SM and contact element PIN and by using measuring parameter values of second measuring parameters the extent of the contact area CTA is determined sufficiently precisely.

Examples for the above-mentioned first measuring parameters are in particular the measuring parameters, which designate a meniscus of a solder joint and/or solder material arranged laterally at the contact element PIN (side fillets).

A single measuring parameter can be sufficient to form an information which designates a probability of greater than 50% for the existence of a galvanic contact between solder material SM and contact element PIN. Several first measuring parameters can be used in order to improve the quality of this information.

The extent of the contact area CTA is determined by means of a piece of information which designates a longitudinal extent ml of the solder joint SJ, SJREF and/or a width extent b of the solder joint SJ and/or a valley width v of a cross-section of the solder joint SJ and/or a first height difference hp between a vertex point heel and a valley point pad of the solder joint and/or a second height difference phd between the valley point pad of the solder joint SJ and the substrate BOARD and/or a fall neg in an edge region of the solder joint SJ and/or a rise sl in an edge region of the solder joint SJ and/or a quantity of material d in a predefinable region of the solder joint SJ.

Further measuring parameters are given at the end of the description (APPENDIX A).

Process steps to be carried out before the solder joint SJ is tested are carried out with a time offset. In particular measuring parameter values can be supplied to the data processing device C (FIG. 1) from an external memory. In this case the circuit arrangement according to the invention does not need a device I.

An advantageous embodiment of the process according to the invention for testing a solder joint SJ for freedom from faults by means of X-rays, is characterized in that the solder joint SJ is tested for the extent of a contact area CTA formed between the solder material SM and contact element PIN, whereby the extent of the contact area CTA formed between the solder material SM and contact element PIN is compared with a predefinable contact-area reference value CTAREF. Finally the solder joint SJ is judged to be a fault-free solder joint SJG or a faulty solder joint SJB depending on the result of the comparison.

An item of information which designates a probability of the existence of an electrical contact between the solder material SM and contact element PIN is formed as a function of measuring parameter values of first measuring parameters PM1, and the extent of the contact area CTA can be determined by means of measuring parameter values of one or more second measuring parameters PM2.

The above-mentioned first and second measuring parameters can also be used in this embodiment of the process according to the invention.

As a result of the test, either a first item of information INFSJG is formed, which designates the freedom from faults of a tested, fault-free solder joint SJ, and/or a second item of information INFSJB, which designates the lack of freedom from faults of a tested, faulty solder joint SJ. The first item of information INFSJG and/or the second item of information INFSJB is (are) used to control a process for producing solder joints.

In general the process for testing solder joints according to the invention is characterized in that the solder-joint-specific quality information and/or solder-joint-specific measurement information which designates measured physical measuring parameters of tested solder joints is correlated with grey-value parameters from X-ray images of the solder joints and, on the basis of the correlation, criteria for the formation of rules for measuring the solder joints to be tested are generated.

In general the circuit arrangement according to the invention comprises a control means CPU (FIG. 1) to which a control program defined by the process according to the invention is assigned.

In FIG. 7 on the x-axis measuring parameter values PARiVALSJGREF of fault-free reference solder joints of identical type to one or more solder joints SJ to be tested are given for each of the measuring parameters PAR1, PAR2 and PAR3 (right hand side) are given.

On the y-axis the respective number of the corresponding measuring parameter values are given.

Furthermore on the x-axis a fault actual-value range DFAi on the left-hand side in respect of the measuring parameter values PARiVALSIGREF of the fault-free reference solder joints is indicated, which has an upper range limit value UVDFAi and a lower range limit LVDFAi. The upper range limit UVDFAi is equal with a first threshold value Ti1 which is to be compared with the measuring parameter value PARVALSJ of the solder joint SJ to be tested.

A second threshold Ti2 is arranged distanced by a threshold value deviation (a, b, c) from the first threshold Ti1, whereby the second threshold Ti2 is compared with the measuring parameter value PARVALSJ of the solder joint SJ to be tested according to a preferred embodiment of the process according to the invention.

In FIG. 7 the measuring parameter value of a faulty reference solder joint SJBREF is arranged in the respective fault actual-value range DFA. When 100% is assigned to the fault actual-value range, the arrangement of the measuring parameter value of the faulty reference solder joint SJBREF can be expressed in %, whereby 100% is assigned to the upper range limiting value UVDFA or to the lower range limiting value LVDFA. In FIG. 7a PAR3VALSJBREF is 30%, PAR2VALSJBREF is 50% and PAR1VALSJBREF is 10%, in respect of the lower range limiting value. Correspondingly, PAR3VALSJBREF is 70%, PAR1VALSJBREF is 50%, PAR1VALSJBREF is 90%, in respect of the upper range limiting value.

Since PAR3VALSJBREF (=70%)>PAR2VALSJBREF (=50%)>PAR1VALSJBREF (=10%) in respect of the lower range limiting value LVDFA, at least the measuring parameter PAR3 will be used for the test of the solder joint SJ or for the detection/filtering of a special solder joint defect type, the measuring parameterPAR2 will also be used where applicable.

Assuming that 5 measuring parameters are selected from, e.g., 7 measuring parameters PAR1, . . . , PAR7 to which measuring parameter values PAR1VALSJBREF, . . . , PAR7VALSJBREF are assigned, whereby PAR7VALSJBREF>PAR1VALSJBREF>PAR2VALSJBREF>PAR3VALSJBREF=PAR5VALSJBREF>PAR6VALSJBREF>PAR4VALSJBREF, then measuring parameters PAR7, PAR1, PAR2, PAR3 and PAR5 are used for the test of the solder joint SJ or for the detection/filtering of a special solder joint defect type.

In FIG. 8 a rule editor of the circuit arrangement SJTD according to the invention is represented by means of 5 windows, each of which shows for each measuring parameter value of fault-free reference solder joints of a measuring parameter and a fault actual-value range. The fault actual-value range is shown as a grey area in the windows. In the upper window the fault actual-value range is arranged on the right hand side next to the measuring parameter values of fault-free reference solder joints, while in the windows arranged below, the respective fault actual-value range is arranged on the left hand side next to the measuring parameter values of fault-free reference solder joints.

In the top window measuring parameter values of the measuring parameter "width of the soldered area" are shown and in the further windows measuring parameter values of the measuring parameter "heel solder", "heel pad delta" (difference in height between meniscus and circuit board area), "measured length of the soldered area" and "toe pad delta" are shown. The exterior curve shows the distribution of the measuring values in respect of, e.g., several circuit boards. The three vertical lines in the upper part of the windows represent the average value and +/− standard deviation.

As already described the device I measures physical parameters (measuring parameters PAR in FIGS. 7 and 8; APPENDICES A and B at the end of the description) of the solder joints as for example the topography (geometrical dimensions) and/or the inner structure (e.g.: air inclusions, cracks) of solder joints or the solder material volume and generates corresponding measurement information (for example measuring parameter values PAR1VALSGREF of fault-free reference solder joints SJGREF, measuring parameter values PAR1VALSJBREF of faulty reference solder joints SJBREF, measuring parameter values PAR1VALSJ of solder joints SJ in FIG. 7). A plurality of measurement information items can be generated for each solder joint, in particular for each reference solder joint, as will be described.

To this end, the device I has the appropriate data-processing functionality; as an alternative to this, the corresponding data processing is carried out by the device C.

Overall, the arrangement illustrated in FIG. 1 constitutes a control or regulation arrangement with which printed circuit boards may be pre-treated with regard to their population with electronic components, may be populated, soldered and checked for their quality.

The solder-joint-specific quality information and/or solder-joint-specific measured value information which characterizes measured physical parameters of checked solder joints is used for the repair of checked, defective solder joints, for the verification of checked solder joints and/or for the control of the production of further solder joints on-line, that is to say in the continuous production process in which the solder joints are tested.

For instance, the solder volume of the solder joints and/or the height at least of one meniscus of the solder joints and/or dimensions of the contact area of the solder joints on the printed circuit board are measured, and the measured value information is formed from these measured values.

In this connection, provision is further made that, using the solder-joint-specific quality information and/or using the solder-joint-specific measured value information, a test is carried out for defective solder joints as to what type of defect is present. This testing may be performed by means of algorithms which are known per se and which are described, for example, in EP 0 236 001 B1. These defect types include, for example, "cold solder joint" and "incorrect positioning of a solder joint".

The device I forms so-called tag files, that is to say files in which the defect messages for one printed circuit board are contained.

The control program that is assigned to the controller CPU of the data processing device C allocates the defects detected to a defect type or a defect class in each case. For instance, the defect classes "solder paste defect", "population defect" and "soldering defect" are provided.

For example, the defects "deficient solder" and "excessive solder" are defects of the defect class "solder paste defect"; the defect "offset of a populated component" is a defect from the defect class "population defect"; and "wetting defect" (solder not correctly fused with the pin) is a defect from the defect class "soldering defect".

A defective solder joint may have a plurality of defects, so that such a solder joint may be assigned to a plurality of defect types or defect classes.

Depending on the respective defect class (solder paste defect, population defect, soldering defect), the data processing device supplies the device L, B or R with control information. If the data-processing device has detected, for example, a defect from the defect class "solder paste defect", it adjusts the device L. If the data processing device has detected, for example, a defect from the defect class "solder paste defect" and, in addition, a defect from the defect class "population defect", it adjusts the device L and the device B. The control information may comprise, for example, a defect-warning signal, which can be displayed on the devices L, B or R or on the associated monitors, or may comprise data, which modify the operation of the respective device. Examples of this are changes to the quantity of solder paste supplied in each case and changes to the temperature of the soldering means.

A defect may have several causes. For instance, the defect "deficient solder" may arise from a "solder paste defect" (=defect during the application of solder paste) and from a "population defect" (=defect during population, for example component is offset in such a way that only part of the area (lead) that is normally to be wetted of the component is supplied with sufficient solder), so that in this case the defect "deficient solder" has the two defect classes "solder paste defect" and "population defect" assigned to it.

For predefinable points on the printed circuit board to be tested, the device I forms at least one measured value, it also being possible for provision to be made for a plurality of measured values to be formed for a specific point on the printed circuit board. For each predefinable solder joint, the device I provides an item of measured value information or a combination ("rule") of several items of measured value information to the data processing device C.

The control program that is assigned to the controller CPU of the data processing device C is configured in such a way that each item of measured value information is compared with a desired value (defect limit value) or with a lower and upper limit of a permissible range. The desired values (defect limit values) or the limits of permissible regions are predefinable or have a fixed relationship with a statistical mean which has been given by a process recognized to be good. Provision may be made for the limit values to be able to deviate only by predefinable ranges in a measured-value specific manner from the respective statistical mean of a process recognized to be good.

If a combination of items of measured value information consists of three items of measured value information, for example, then each of the three items of measured value information is compared with its associated desired value (defect limit value), which must neither be overshot nor undershot, or with the lower and upper limit value of a permissible range.

If the result is that each item of measured value information of the combination of items of measured value information does not overshoot the associated desired value which must not be overshot, or does not undershoot the associated desired value which must not be undershot, or lies within the limits of the permissible range, then the ("first") solder-joint-specific item of quality information "solder joint defect free" is formed. Otherwise, the ("second") solder-joint-specific item of quality information "solder joint defective" is formed.

If the second item of quality information "solder joint defective" is to be formed, that is to say the measured value overshoots a permissible upper limit value or if it undershoots a permissible lower limit value, then, in relation to the relevant solder joint, that item of measured value information that has the greatest relative deviation from the respectively associated limit value is ascertained.

If the result is that, for example, the second item of measured value information of the combination of items of measured value information has the relatively greatest deviation from its associated desired value, one and only one of the devices L, B, D or R is adjusted, depending on this item of measured value information.

Provision may be made for those two items of measured value information of a combination of items of measured value information, which have the relatively greatest deviations from their respective defect limit value in each case to be ascertained. If, in the example of the combination of items of measured value information comprising three items of measured value information, this applies to the first and the second items of measured value information, then depending on these two items of measured value information (first and second items of measured value information), then it is only the device L, B, D or R which is responsible for the occurrence of the relevant defect which is adjusted. It is also possible for a plurality of devices L, B, D, R to be the cause of defects for the occurrence of combinations of items of measured value information. In this case, the appropriate devices are adjusted.

Furthermore, it is also possible for three and more items of measured value information of a combination of items of measured value information to be evaluated in this way, in order in each case to adjust those devices L, B, D or R, which are responsible for the respective defect.

The defect limit or desired values are predefinable and preferably correspond to the statistical means of a process recognized to be good; however, the defect limit or desired values may also deviate from these means.

If, for example, the width of a predefinable solder joint is x millimetres as a statistical mean (at the peak of the Gaussian distribution), then it is possible for x+a, x−b, 1.1x, etc. to be provided as defect limit values. It is thus possible for typical defect characteristics to be filtered out. x may be 20 millimetres and the predefinable lower defect limit value may be 16 millimetres (x=4 millimetres). A current measured value at 18 millimetres is then judged as adequate. The relative deviation of the current measured value from the defect limit value is then (18−16)/18×100% 11.11%.

As an example, a combination of items of measured value information (combination of measuring parameter values of fault-free reference solder joints belonging to the same type as one or several solder joints Sj to be tested later on) consists of the following three items of measured value information (PARiVALSJGREF for I=1, 2, 3; see FIG. 7)
Measured value information item 1:
  measured width (measured solder joint width)=22 millimetres
Measured value information item 2:
  heel solder (amount of solder) corresponding to 6000 standardized grey-value components in a defined testing window
Measured value information item 3:
  heel pad delta (solder meniscus height)=1500 micrometers.

The statistical means are, for example, in the case of measured value information item 1:
  20 millimetres
in the case of measured value information item 2:
  10,000 standardized grey-value components
in the case of measured value information item 3:
  3000 micrometers.

Hence, the greatest relative deviation results for the measured value information item 3 or measuring parameter PAR3 respectively. Therefore measuring parameter PAR3 is used for a rule according to which solder joints Sj will be tested at a later point of time.

This measured value information item 3 is assigned a first item of information which identifies the defects "soldering defect" and "solder paste defect". Using the first item of information, the devices L and R are adjusted.

If, in the case of this example, the two items of measured value information having the greatest relative deviations are ascertained, then these are the measured value information item 3 and the measured value information item 2. This combination of the measured value information items 3 and 2 is assigned a second item of information, which identifies the defect "soldering defect". Using this second item of information, the device R is adjusted.

If all three items of measured value information from the combination are evaluated, this combination is assigned a third item of information, which likewise identifies the defect "soldering defect". Using the third item of information, the device R is likewise adjusted.

The first, second and third items of information firstly indicate which of the devices L, B, D or R is adjusted. In addition, the first, second and third items of information in each case indicate a controlled variable, that is to say operational parameter or operational parameter changes of the respective device (for example, an increase or reduction in the quantity of solder paste to be applied, an increase or reduction in the solder to be applied).

The three defect classes "population defect", "solder paste defect" and "soldering defect" have a plurality (for example the following) defect types assigned to them:

| | |
|---|---|
| "Wet.Gullw. | A", (wetting of gullwing) |
| "Wet.J-leg | B", (wetting of J-leg) |
| "Wet.quad.SMD | C", (wetting of cuboidal SMD) |
| "SMD_offset | D", |
| "other_sol_def. | E", |

-continued

| | |
|---|---|
| "not_soldered | F", |
| "solder_bridge | G", |
| "bent_away/up | H", (connecting pin bent away/bent up) |
| "SMD_offset | I", |
| "other_sol_def. | J", |
| "solder_beads | K", |
| "INSUFF_TOE | L", (thin solder joint) |
| "SMD_bubble | V", (solder bubble) |

In addition, provision may be made for the detected defects or items of measured value information to be assigned to a defect type—such as listed above, for example—and for the defect types to be assigned to a defect class (solder paste defect, population defect, soldering defect).

The solder-joint-specific quality information and/or the solder-joint-specific measured value information which characterizes the measured physical parameters of checked solder joints, and/or statistical information about the frequency of occurrence of defects are displayed on the monitors LMON, BMON, RMON which are assigned to the devices L, B and R.

The data processing device C and the repair workstation SST may, for example, be designed in the following two variants:

1. PC variants

| | |
|---|---|
| CPU | HP Vectra VL2 4/66 |
| | HP Vectra VL2 5/60 |
| Main memory | 24 MB |
| Hard disk | 500 MB |
| Swap | 60 MB |
| Graphics card | Ultra VGA 1024x768 pixels |
| Monitor | 15" or 17" |
| Operating system | Solaris x86 2.4 |
| Network card | 16-bit BNC, TP, AOI |
| Options | |
| Input | Numeric keypad |
| | Trackball |
| | RS-232 bar-code scanner |
| Light pointer | Heeb OM-500 |
| | Royonic 500 |
| Printer | HP DeskJet 1200C/PS |
| | HP LaserJet 5MP |
| Data backup | Magnetic tape (QIC or DAT) |
| | Magneto-optical disk drives |

2. Workstation variants

| | |
|---|---|
| CPU | Sun SparcStation 4 |
| | Sun SparcStation 5 |
| Main memory | 32 MB |
| Hard disk | 1 GB |
| Swap | 60 MB |
| Graphics card | 1024x768, 1152x900 pixels |
| Monitor | 15" or 17" |
| Operating system | Solaris 2.4 |
| Network card | incorporated |
| Options | |
| Input | 3 ½" floppy disk drive |
| | Numeric keypad |
| | RS-232 bar-code scanner |
| Light pointer | Heeb OM-500 |
| | Royonic 500 |
| Printer | HP DeskJet 1200C/PS |
| | HP LaserJet 5MP |

| Data backup | Magnetic tape (QIC or DAT) |
|---|---|
| | Magneto-optical disk drives |

The control program defining the process according to the invention is, for example, a UNIX application which is mounted on the Solaris operating system from SunSoft.

The control program realizes, inter alias:

a) a display of the X-ray inspection results generated by the device I (for example FIG. 8);

b) a display of the defects found during the X-ray inspection, step by step in a graphic representation of the printed circuit board layout;

c) a display of the defects found during the X-ray inspection, step by step with the aid of a laser/light pointer on the original printed circuit board;

d) a display of defects (accumulation of defects at one or more points on the printed circuit board) in a graphic representation of the printed circuit board layout;

e) verification, acknowledgement and further processing of the defects found during the X-ray inspection, if necessary step by step by an operator of the repair workstation SST, using a dialogue menu; and f) storage of processed defect data as an interface to a program module or to quality management systems.

The above-mentioned elements of the control program are described below:

a) display of the X-ray inspection results generated by the device I in text form.

This display is produced on the SMON monitor of the repair workstation SST.

The program working area comprises a main window with a menu bar. Further windows may be superimposed.

The menu bar comprises the following menus with the options:

| • File | File functions |
|---|---|
| Editor | Call up a text editor |
| Exit | Exit from program |
| • Operating mode | Select operating modes |
| Individual defect | Individual defect display |
| Defect overview | Display of the defect overview |
| X-ray image | Display of the X-ray image |
| • Configuration | Configuration settings |
| Light/laser pointer> | Select the light/laser pointer |
| Royonic 500 | Royonic 500 light pointer |
| Heeb laser | Heeb LL-2A or OM-500 |
| Operating mode> | Setting the standard operating mode (s) |
| Individual defect | Individual defect display |
| Defect overview | Defect overview |
| X-ray image | X-ray image window |
| File paths> | File path specification |
| CXI tag files | Path to the CXI tag files |
| X-ray image files | Path to the X-ray views |
| CAD files | Path to the CAD files |
| Results files | Path to the results files |
| Defect type reference | Path to the defect type reference file |
| Verification dialogue> | |
| GOOD boards auto. | Automatically accept defect-free boards |
| Options> | Option menu for various settings |
| Symbol bar | Superimpose and hide symbol bar |
| Save on exit | Save settings on exit |

The above-described menu bar is adapted appropriately in the event of changed or additional operating steps.

b) Display of the defects found during the X-ray inspection, step by step in a graphic representation of the printed circuit board layout b1) Operating mode: individual defect display The control of the individual defect display by the operator of the repair workstation SST is carried out using a dialogue window, which contains the elements Header, Option group Display, Option group Page, Defect list, Buttons, Next, Back, True defect, Pseudo defect, New defect, Change defect type, Next component, Done, Abort In the "Header", the data from the top of the data from the X-ray system I are displayed.

Using the "Option group Display", the operator is able to select the display forms for the individual defect display. The options available are "Layout", for the representation of the graphical printed circuit board layout on the monitor, and "Pointer", for the display on the original printed circuit board with a light/laser pointer.

With the aid of the "Option group Page", the side of the printed circuit board that is displayed is selected. Those available are upper side and lower side.

The "defect list" contains all the defects on the printed circuit board that were found by the X-ray system or added by the operator. The defect which is currently displayed in the printed circuit board layout and/or indicated by the light/laser pointer is highlighted in the defect list.

The button "Next" displays the next defect in the defect list in the printed circuit board layout and/or using the light/laser pointer.

The button "Back" displays the preceding defect in the defect list in the printed circuit board layout and/or using the light/laser pointer.

The button "True defect" marks the current defect as a true defect.

The button "Pseudo defect" marks the current defect as a pseudo defect.

The button "New defect" inserts a new defect into the list and shows the defect in the printed circuit board layout and/or using the light/laser pointer.

The button "Change defect type" permits the defect type of a defect that has already been marked to be changed again.

The button "Next component" jumps to the next component in the defect list. If this button is pressed, the individual defects are erased, and the defect code for the total component defects is entered in the results file.

The button "Done" or the button "Enter" after the last defect entry enters the marked true defects and the marked pseudo defects in the results file and terminates the verification operation for this subassembly. In the event of a premature abort, an abort message is entered in the results file as the last line (see also the "Abort" button).

The button "Abort" closes the dialogue window and the window with the graphical printed circuit board layout and/or moves the light/laser pointer into a rest position. An abort message is entered in the results file (see below) as the last line.

Via a standardized software interface, the selected defect is transferred to the program module for the display in the graphical printed circuit board layout and using the light/laser pointer.

Figures 10, 11:
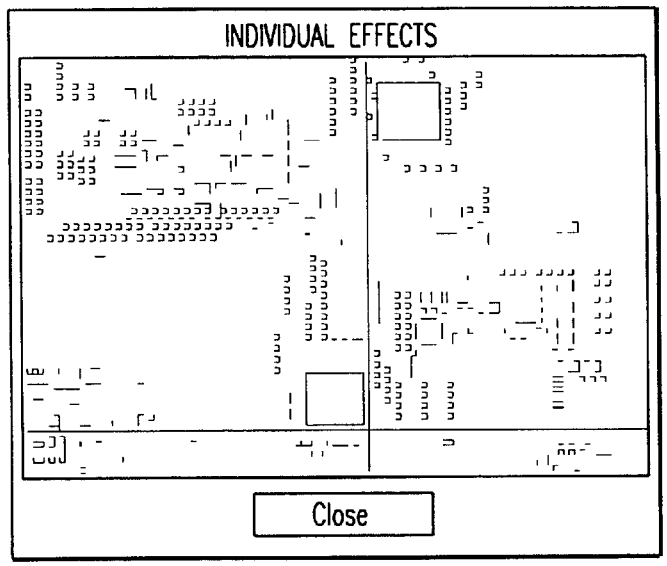
FIG. 10 shows a monitor display, formed within the context of the process according to the invention, of an individual defect.
FIG. 11 shows a monitor display, formed within the context of the process according to the invention, of a defect list.

If the display of the printed circuit board layout is activated, then each defect in the defect list is displayed by means of a marking in a graphical printed circuit board layout, which is produced from CAD data that describe the printed circuit board. A display is illustrated in FIG. 10, it being the case that, for example, the solder joint marked by the (external) arrow in the actual screen display is assigned a marking which cannot be seen in FIG. 10.

In a standard setting, all the subassemblies of the printed circuit board are displayed in the graphical layout. Defect data are accepted via a standardized software interface, and the appropriate defects are displayed. Defects are highlighted in colour.

It is possible to display the entire printed circuit board or only a detail, preferably on an enlarged scale.

b2) Operating mode: defect overview

This operating mode makes it possible to display the marked true defects from the defect list, together or separated by defects, on a graphical representation of the printed circuit board layout.

The defects which the device I detects are assigned to the defect types "population defect", "soldering defect" and "solder paste defect". "Population defects" are displayed in blue, "soldering defects" in yellow and "solder paste defects" in green.

The side (upper side/lower side) of the printed circuit board on which the components are located is indicated in the window.

Illustrated in FIG. 11 is an example of a defect list displayed on the screen.

b3) Operating mode: X-ray image display

Figure 12:
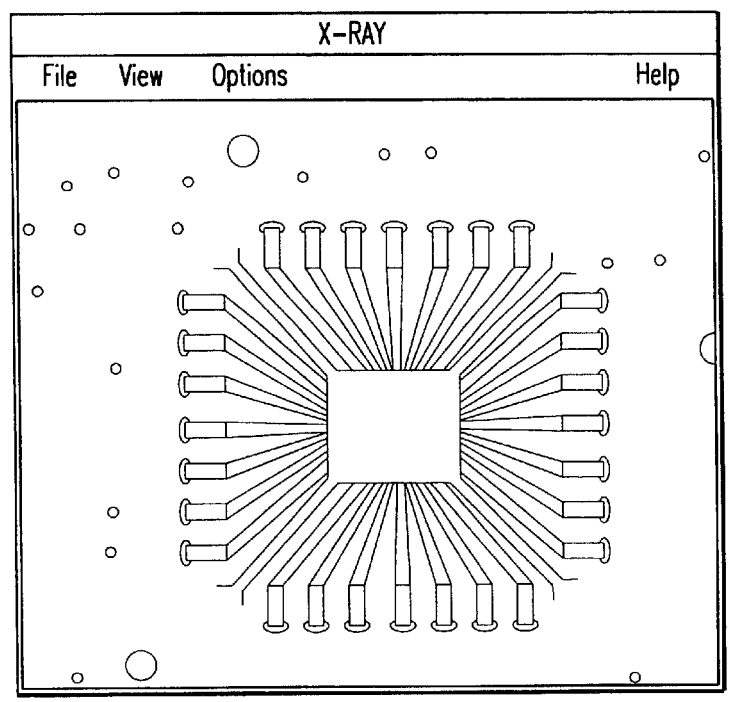
FIG. 12 shows a monitor display, formed within the context of the process according to the invention, of an X-ray image of a printed circuit board having solder joints, whereby a faulty solder joint is marked.

In a separate window, it is possible for the X-ray image matching the data generated by the device I to be displayed. An example of such a window is illustrated in FIG. 12, a defective solder joint on the right in the window being marked by a square frame. It is optionally possible for the complete components list of the image to be superimposed on this window.

c) Display of the defects found during the X-ray inspection, step by step with the aid of a laser/light pointer on the original printed circuit board;

If the display using the light/laser pointer is activated in the dialogue window, then the defect is indicated on the original printed circuit board using a point of light. For example, it is possible to use the Royonic light pointer 500 or Heeb Laserlite LL-2-A or 500 light/laser pointers.

d) Display of defects (accumulation of defects at one or more points on the printed circuit board) in a graphical representation of the printed circuit board layout.

Figure 13:
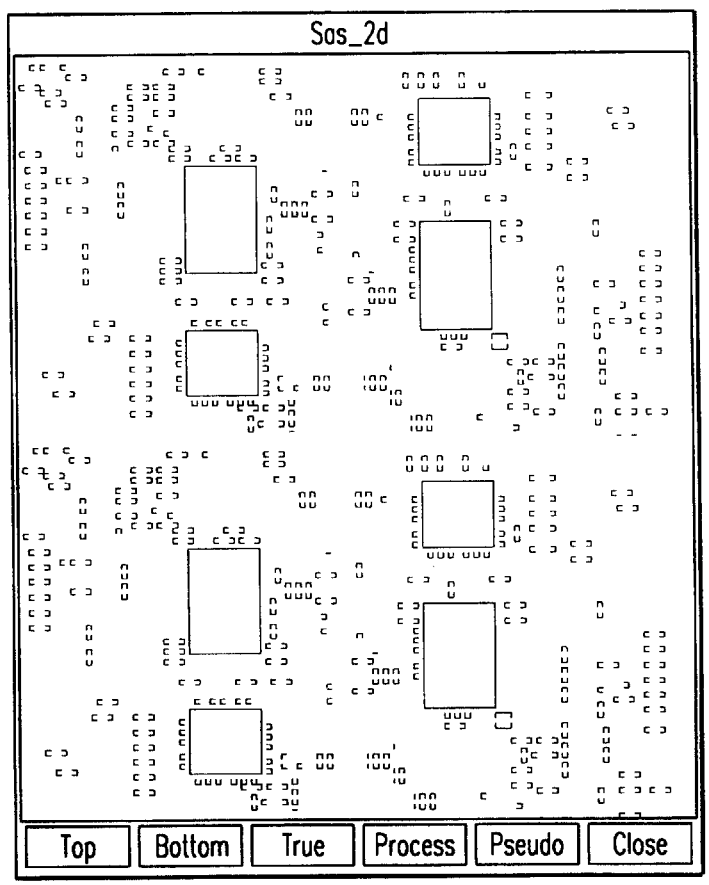
FIG. 13 shows a monitor display, formed within the context of the process according to the invention, of defects (accumulation of defects at one or more points on the printed circuit board) in a graphic representation of the printed circuit board layout.

An example of a display of this type is illustrated in FIG. 13, it not being possible in FIG. 13 to recognize the actual defect data which, in the actual screen display, are assigned adjacent to the associated solder joints.

Figure 14:
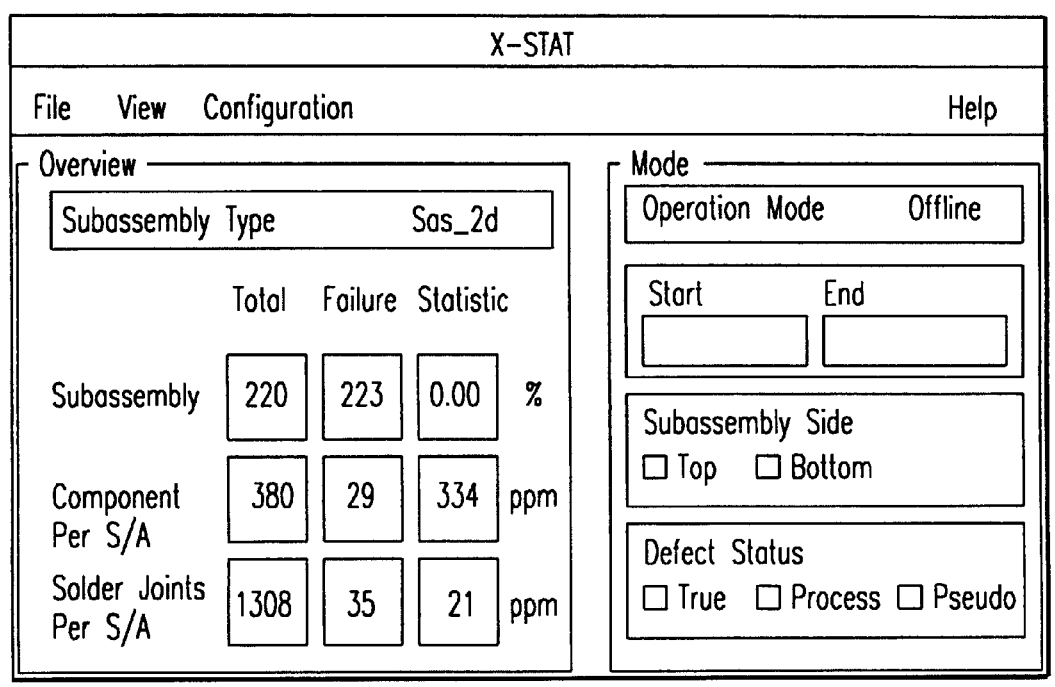
Figure 15:
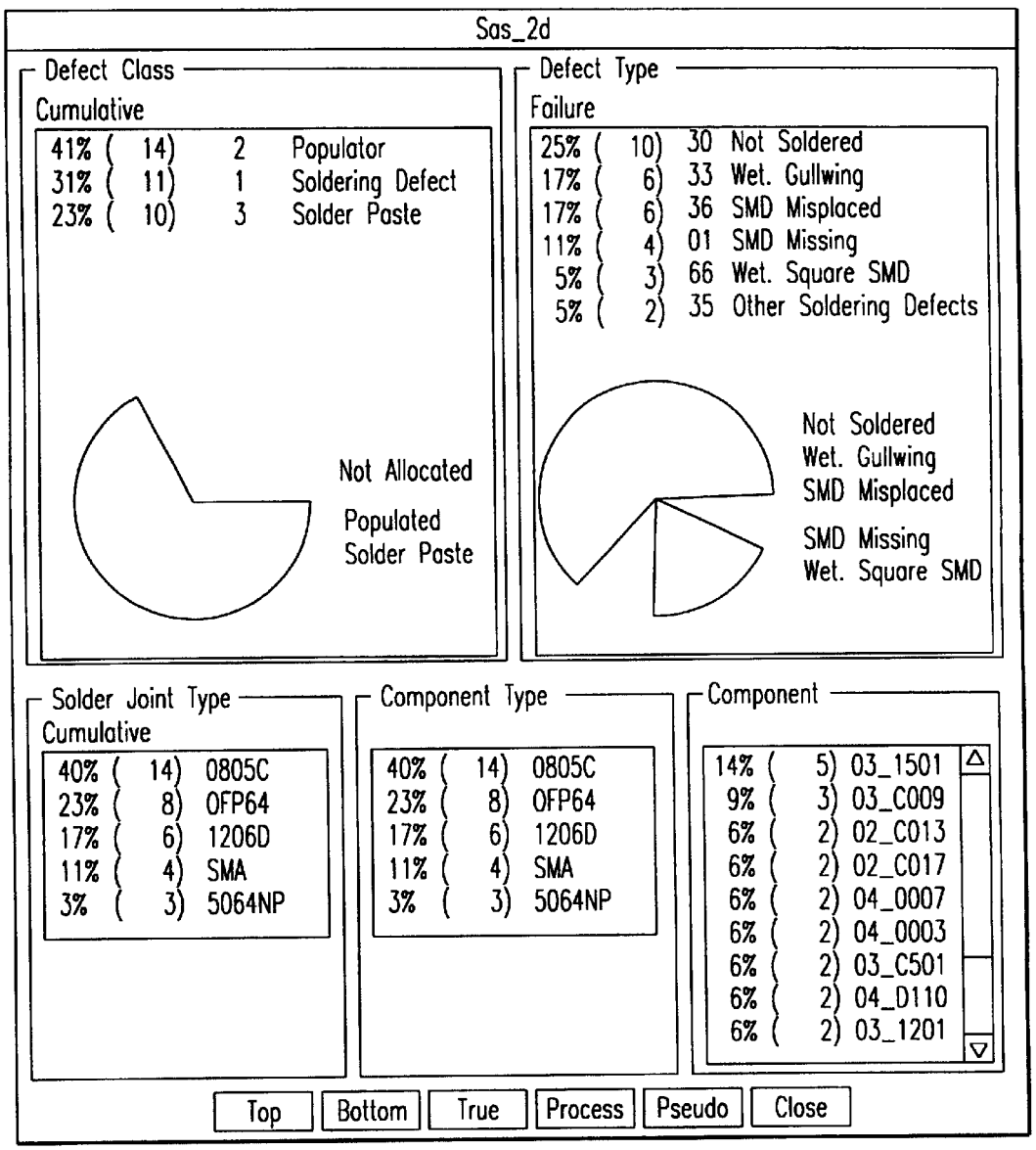

Further displays of defects in a statistical evaluation are illustrated in FIGS. 14, 15 and 16.

e) Verification, acknowledgement and further processing of the defects found during the X-ray inspection, optionally step by step by an operator of the repair workstation SST using a dialogue menu.

The sequence of a cycle in conjunction with the verification of defect-free printed circuit boards, and the repair of defective printed circuit boards, is described below, and is also illustrated in FIG. 18.

For the verification and repair of printed circuit boards, it is necessary for the individual defect display operating mode to be activated. A repair cycle begins with reading the printed circuit board number using a bar-code reading pen. Alternatively, the repair may also begin with the selection of a defect tag file via keyboard or mouse.

On the basis of the printed circuit board number read, the associated tag file for the printed circuit board is sought and opened, and the header and the defect list are read. If a defect-free printed circuit board is involved, then a distinction is made between two cases, depending on the GOOD_BOARDS switch:

GOOD_BOARDS=AUTO

A message is displayed to say that the printed circuit board is defect free, and an entry in the results file is automatically generated, or a new results file is created, in which the defect-free printed circuit board is noted.

GOOD_BOARDS=MANU

The procedure continues as in the case of defective printed circuit boards, with the exception that the defect list is empty.

In the case of a defective printed circuit board, on the basis of the subassembly identification number contained in the header of the tag file, the CAD files are sought and opened and the geometric data of the subassembly are read. If the subassembly identification number of the current printed circuit board is identical with that previously tested, then the renewed reading of the geometric data is omitted.

The defect list is displayed in the dialogue window, the first defect is marked and indicated on the printed circuit board layout on the screen and/or using the light/laser pointer.

With the aid of the switching areas in the dialogue window that were described in the section "individual defect display", the defects in the list can then be classified and marked by the operator. After a defect has been marked, a jump is automatically made to the next defect. If the operator has marked (processed) all the defects in the list, or marked them as a total defect using "next component", then these defects are entered in the results file.

Following the processing of the board, the test files relating to the printed circuit board (I-tag files, X-ray images) are removed, if a switch DEL_TAG=On is set. The standard value is DEL_TAG=Off.

If there is no test tag available for the current board, the results file is looked through following an entry for this board or the corresponding directory is looked through for a results file for this board, and the following is done:

Output of a defect message if the board is also not present in the results file or if no dedicated results file exists for this board.

If a defect-free board is concerned, from which the tag file is available, then the procedure is as described above, depending on the GOOD_BOARDS switch.

If the renewed processing of the board is concerned (no tag file, but entry in the results file or a dedicated results file), then the further operation is affected by the REWORK_BOARDS switch. If the entry in the configuration file is REWORK_BOARDS=On, then the printed circuit board can be processed once more using the defect data from the results file. If, on the other hand, the entry is REWORK_BOARDS=Off, then a message is output that repeated processing is not possible.

f) Storage of processed defect data as interface to a program module or to quality management systems.

The data processing device C processes, inter alia, population data, using the following fields:

| Field name | Data format | Description |
|---|---|---|
| Joint | long int | Consecutive number of the solder joint (I to max joint) |
| Pin/Device | long int | Consecutive number of the pin per component (1 to max pin) |
| Pin X | long int | X-coordinate of the pin related to the board origin |
| Pin Y | long int | Y-coordinate of the pin related to the board origin |
| Pad X | long int | Pad length in X-direction |
| Pad Y | long int | Pad length in Y-direction |
| Side | char | Subassembly side (T ç B) |
| Device name | char [15] | Designation of the component (without '\0') |
| Device type | char [25] | Designation of the component type (without '\0') |
| View | long int | Consecutive number of the view (1 to no of views) |
| View X | long int | X-coordinate of the pin in relation to the view |
| View Y | long int | Y-coordinate of the pin in relation to the view |

In addition, the data processing device C processes a defect type reference file.

As already described, each defect detected by the device I is assigned a defect class "population defect", "soldering defect" and "solder paste defect". The contents of the file are organized into individual data sets having, for example, four data fields. Each line of the file describes one reference. The fields have the following meanings:

| Field name | Field length | Description |
|---|---|---|
| Defect | 3 characters (long) | Defect number |
| Defect message | 20 characters | As per defect tag |
| Defect class | 3 characters (long) | Defect class |
| Defect class message | 20 characters | Message for screen outputs |
| Color | 10 characters | Color with which this defect is displayed on the screen |
| Symbol | 10 characters | Symbol that is used to display the defect on the light/laser pointer |

An example of a defect type reference file is configured as follows:

| #Defect type | Defect class | Color | Symbol |
|---|---|---|---|
| 65;2503 solder link | a;1;soldering defect; | yellow; | point |
| 40;2503_Wet.Gull w. | H;1;soldering defect; | yellow; | point |
| 18;3208 offset row | 2;4;population defect | blue; | arrow |

For each printed circuit board, a dedicated results file may be generated. As an alternative to this, a common results file can be generated for a plurality of processed printed circuit boards, in particular for all processed printed circuit boards. For the two types of results file, each defect generates an entry in this file.

For the subassembly handled, a header dataset is created first, this consisting of the following fields:

| Field name | Field length | Description |
|---|---|---|
| Dataset type | 1 character | always "H" in header line |
| Serial number of the subassembly | 25 characters | as per defect tag or bar-code |
| Blank ID | 2 characters (long) | as per defect tag |
| Subassembly type | 20 characters | as per defect tag |
| Test system ID | 12 characters | as per defect tag |
| Date of inspection | dd:mm:yy | as per defect tag |
| Time of inspection | hh:mm:ss | as per defect tag |
| UserID of tester | 4 characters (long) | as per/etc./passwd file |
| Date of repair | dd:mm:yy | as per system time |
| Time of repair | hh:mm:ss | as per system time |
| Status | 1 character (long) | 0 = no repair; 1, 2...number of repairs |

Adjacent to this header line there follows, for each defect, a data line which consists of the following fields.

| Field name | Field length | Description |
|---|---|---|
| Dataset type | 1 character | always "D" in data line |
| Component name | 15 characters | as per defect tag |
| Pin number | 3 characters (long) | as per defect tag |
| Defect code 1 | 3 characters (long) | as per defect code table |
| Defect code 2 | 3 characters (long) | as per entry by the tester |
| Rule | 2 characters (long) | as per defect tag (DL field) |
| Defect class | 3 characters (long) | as per reference table |
| Defect status | 2 characters (long) | Code (0 = confirmed, 1 = changed, 2 = pseudo) |

The above-described process may be one control program from a plurality of program modules assigned to the controller CPU. The control program, which is preferably of modular construction, may have further program modules which are the subject-matter of the process claims. Each program module can be used on its own or together with one or more other program modules.

A program module of the control program is, as already described, configured in such a way that the X-ray images generated by the device I, or electronic images generated from these and images generated from CAD data and relating to the graphical layout of the printed circuit boards may be displayed on the monitor SMON at the repair workstation SST.

In this case, the X-ray images or the electronic images, as well as the printed circuit board layout images are displayed together with solder-joint-specific measured value information which characterizes measured physical parameters of checked defective solder joints, optionally together with statistical information about the frequency of occurrence of defects. The information is displayed alphanumerically and/or symbolically in the X-ray images.

Figure 19C:
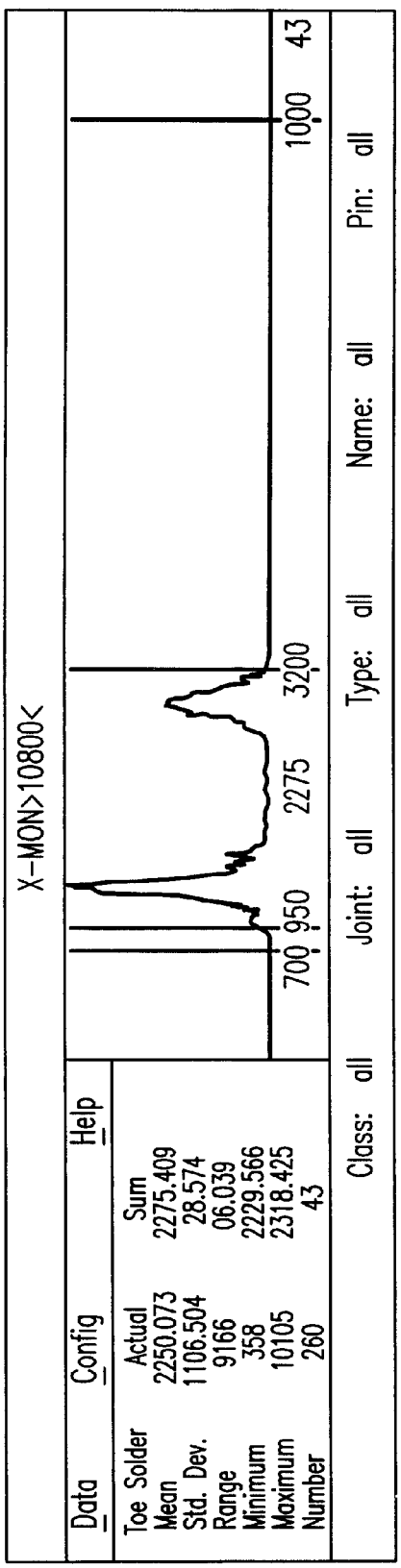
FIGS. 19a–19c show monitor displays, formed within the context of the process according to the invention, of measurements and windows for measurement selection.
Figure 19D:
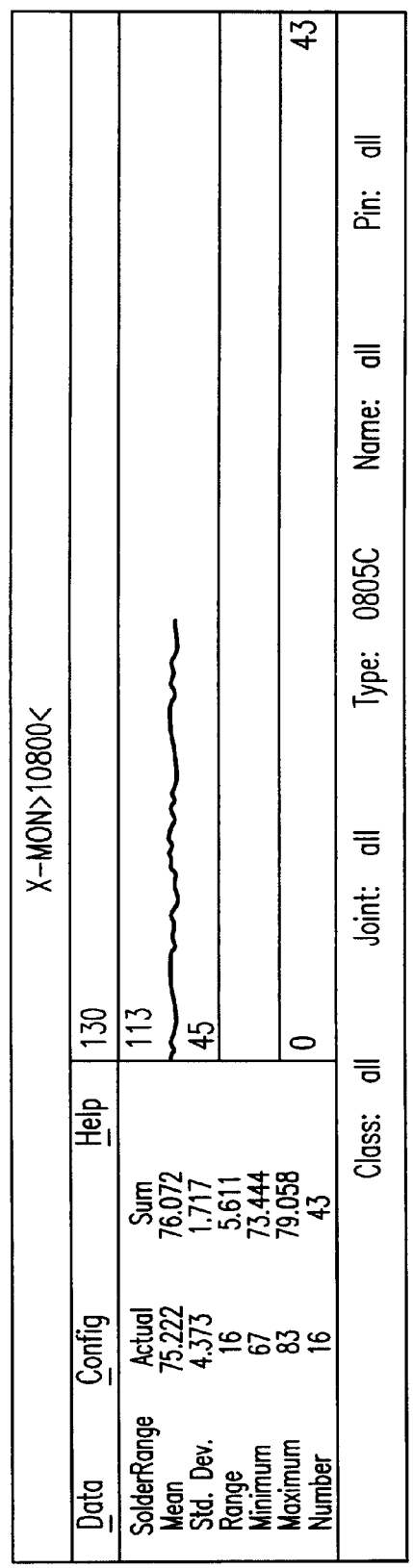
Figure 19E:
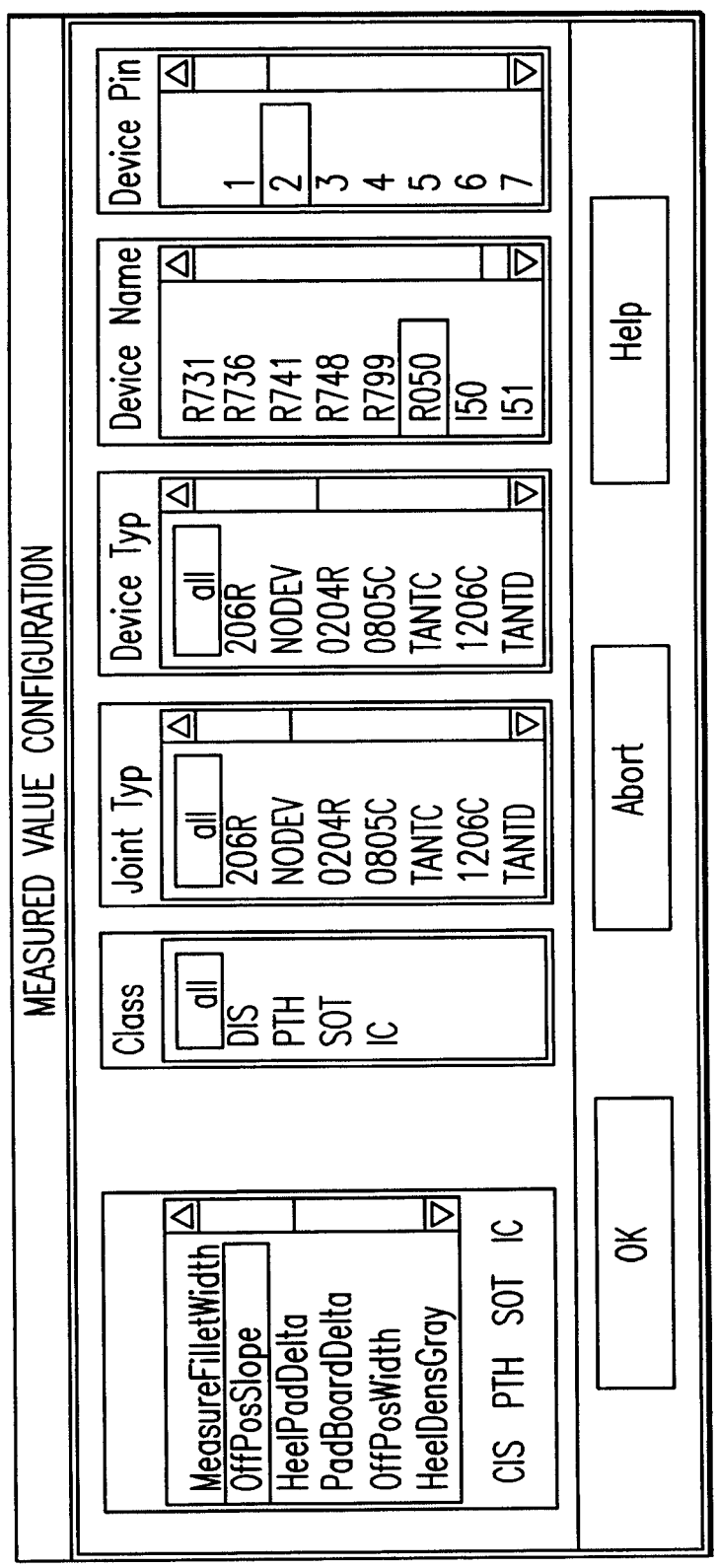
Figure 20:
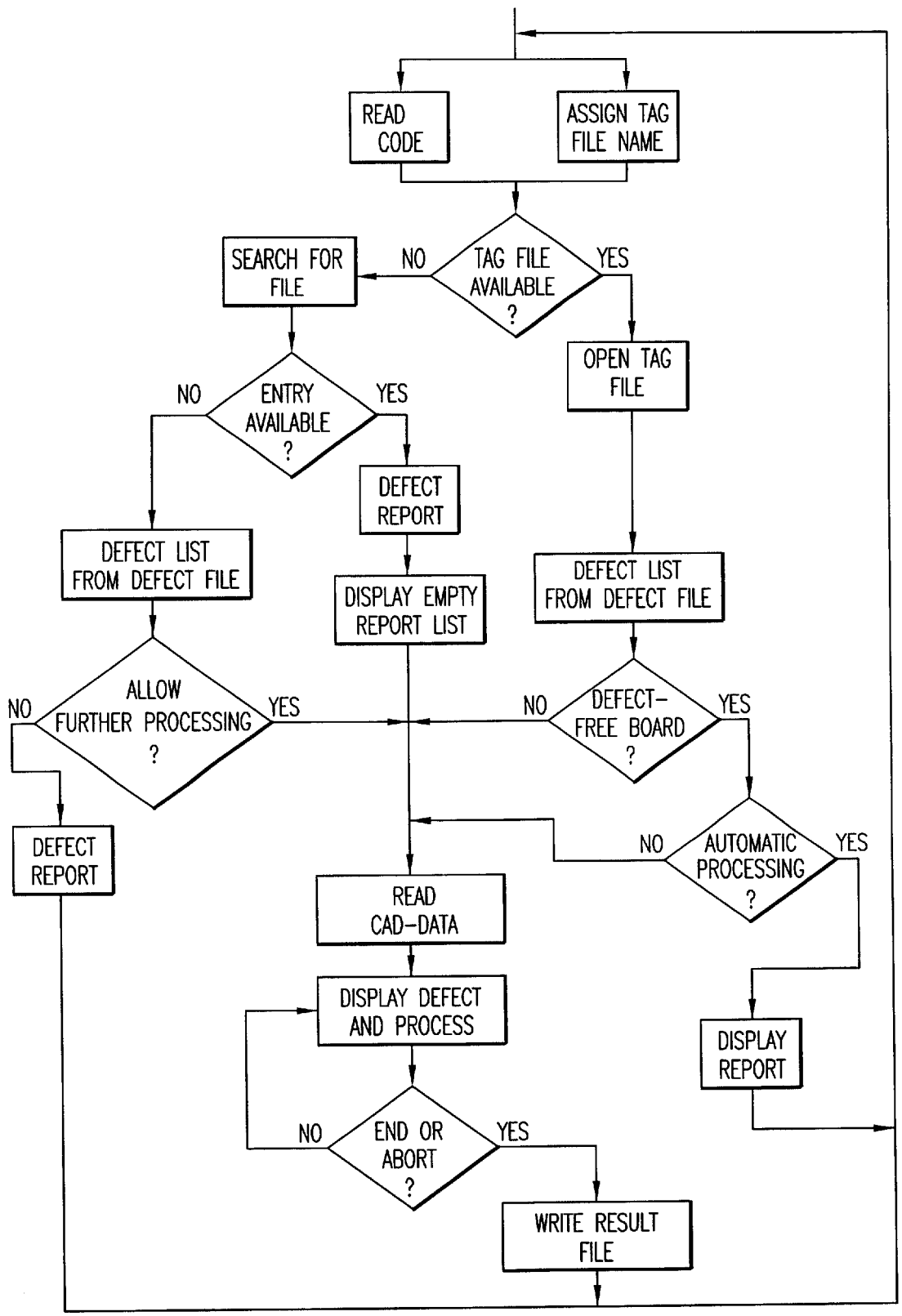
FIG. 20 shows the sequence of a cycle in connection with the verification of fault-free printed circuit boards and the repair of faulty printed circuit boards.

A further program module of the control program is configured in such a way that the solder-joint-specific quality information and/or solder-joint-specific measured value information which characterizes measured physical parameters of checked solder joints, is compared with predefinable production process threshold values and that, depending on the comparison, process control data are formed. For example, the production process threshold value predefined is a specific amount of solder, which is to be applied per predefinable solder joint. If, using a comparison of this production process threshold value or production process reference value with the corresponding solder amount measured value information, the result is that this threshold or reference value is overshot or undershot by a predefinable tolerance range, the data processing device C forms alphanumeric and/or graphical information which describes the reference value and/or the measured value information and/ or the extent of overshooting or undershooting the reference value. Furthermore, the data processing device may determine that (those) device(s) (L, B, R) which cause(s) the overshooting or undershooting of the amounts of solder. This information is fed to the monitor SMON of the repair workstation SST and to the monitor of that device (e.g. R) which is causing the overshooting or undershooting of the amounts of solder. Appropriate screen displays are illustrated in FIG. 19.

Furthermore, the data processing device C may form an item of control information for this device (e.g. R), which effects a change in the operating parameters of this device. If, for example, the reference value is exceeded to a certain extent, then the control information (that is to say process control data) is formed in such a way that the device R reduces the amount of solder per solder joint appropriately. These procedures, which are carried out for the direct control of the continuous production process, may already be carried out on-line before the occurrence of soldering defects, that is to say at times at which "solder joint defect free" quality information is still being formed.

Screen displays in conjunction with the configuration of measured values and of reference values ("upper warning limit", "lower warning limit") are illustrated in FIGS. 19c, 17, 20 and 21.

Using the solder-joint-specific quality information and/or using the solder-joint-specific measured value information, a test is therefore carried out, for solder joints whose physical parameters deviate from the predefinable production process threshold values or reference values, as to which of the first and/or the second and/or the third devices L, B, R this deviation is to be assigned. Depending on this assignment, the first and/or the second and/or the third devices (L, B, R) and, if appropriate, also the associated visual display device (LMON, BMON, RMON) are adjusted using the process control data. The display devices are, in particular, fed with the alphanumeric and/or graphical information that is formed by the data processing device C and which characterizes the reference value and/or the measured value information and/or the extent of the overshooting or undershooting of the reference value.

A further program module is configured in such a way that the solder-joint-specific quality information and/or the solder-joint-specific measured value information which characterizes measured physical parameters of checked solder joints is correlated with grey-value parameters of X-ray images of the solder joints and, on the basis of the correlation, criteria for the formation of the solder-joint-specific quality information and of solder-joint production process threshold values are generated.

That is to say, rules for the formation of the solder-joint-specific quality information and of solder-joint production process threshold values are generated. The starting point is the measured value information from defect-free and defective printed circuit boards, these data being treated statistically, as well as component-specific parameters, which are stored in a scaling library.

As already described, the device I measures physical parameters of the solder joints, for example geometric dimensions or the profile of the solder joints. One profile parameter, or preferably several profile parameters, such as two height points on the meniscus, the difference between these height points or between each of the height points and the lowest point on the solder joint surface, or a vertical cross-sectional area of the solder joint is or are selected. These profile parameters of solder joints of particularly good or particularly poor quality are combined or correlated with grey-value parameters of the X-ray images of the corresponding solder joints. As a result, automatically determined profile parameters and limit values are selected, these forming new decision criteria for future assessments of the quality of solder joints.

Within the context of the process according to the invention, therefore, solder-joint-specific measured value information is evaluated on-line and transmitted to different devices in the production process. X-ray defect images are used on-line at the repair workstation. Quality information, specifically, inter alia, measured value information, are assigned to the individual production steps or the corresponding devices and displayed there. As a result of the feedback of this information, the production process is controlled. Furthermore, layout-oriented statistics are generated on-line. Finally, using component-relevant data and statistically treated measured value information, rules relating to the solder-joint type are defined for the detection of soldering defects and process limit values.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

APPENDIX A

Measuring parameters for the testing of solder joints

| name | abbrev. | description |
| --- | --- | --- |
| measured_length | 1 | length of the solder joint |
| percent-bridged | | percentage of dark areas between pins -> bridges between pins |
| off_pos_width | o | width of pad, pin and solder -> misplaced pins |
| trace-length | tl | length of the solder on the pad outside the toe -> lifted pins |
| with_x_100 | x | exact width of the solder joint (average width of the solder joint*100) |
| heel_solder | h | solder quantity at the heel |
| pad_solder | p | solder quantity on the pad |
| toe_solder | t | solder quantity at the toe |
| valley_solder | v | valley width of the grey value curve of the cross section -> lifted pins |
| max_toe_slope | ts | maximum solder slope at the toe |
| heel_pad_delta | htpd-1 | grey value difference between heel and pad |
| toe_pad_delta | htpd-2 | grey value difference between toe and pad |
| heel_board_delta | hptbd-1 | grey value difference between heel and board |
| pad_board delta | hptbd-2 | grey value difference between pad and board |
| toe_board_delta | hptbd-3 | grey value difference between toe and board |

APPENDIX A-continued

Measuring parameters for the testing of solder joints

| name | abbrev. | description |
|---|---|---|
| toe_heel_dist | th | --- |
| delta_heel_maxes | dh | --- |
| fillet solder | s | sum of the solder quantities of heel and toe |

Measuring parameters for the testing of solder joints
Measuring parameters for the testing of SOT solder joints

| name | abbrev. | description |
|---|---|---|
| measured_length | ml | length of the solder joint |
| measured_width | m | width of the solder joint |
| valley_width | v | valley width of the cross-section grey value curve -> lifted pins |
| off_pos_width | ow | set off (misplacement) of the pin on the pad |
| heel_pad_delta | hp | -> misplaced pins |
| pad_board_delta | pbd | grey value difference between heel and pad |
| neg_fillet_slope | neg | grey value difference between pad and board |
| fillet_slope | sl | negative slope of the grey value curve |
| heel_solder | d | positive slope of the grey value curve |
| heel dens gray | g | solder quantity at the heel |

Measuring parameters for the testing of solder joints contacting discrete components

| name | abbrev. | description |
|---|---|---|
| pack_gray | | grey value of the component -> component not set or wrongly set |
| measured_width | w | width of the solder joint |
| measured_length | l | length of the solder joint |
| neg_fillet_slope | n | negative rise of the grey-value curve transition between solder and component |
| fillet_slope | s | positive rise of the grey-value curve -> rise of the solder at the component |
| measured_fillet_width | fw | measured width at the fillet |
| heel_pad_delta | hpd | grey value difference between heel and pad |
| pad_board_delta | pdb | --- |
| low_slope_distance | sdl | distance between low_slope and slope |
| low_slope_delta | sds | grey value difference between low_slope & slope |
| disc_skew | | angle of the twisted component |
| Ta_polarity_defect | | polarity (in case of tantal capacitors) |
| mom_ratio | m | relation of width and height of the solder joint |
| porosity_signature | p | porosity of the solder joint |
| solder range | r | solder quantity at the solder joint |

APPENDIX B

Reference signs

| | |
|---|---|
| SJ | solder joint |
| PARIVALSJ | measuring parameter value of a solder joint (parameter i) |
| SJG | fault-free solder joint |
| SJB | faulty solder joint |
| SJREF | reference solder joint |
| SJGREF | fault-free reference solder joint |
| j = 1, . . ., n | plurality of fault-free reference solder joints |
| SJBREF | faulty reference solder joint |
| PARiVALSJBREF | measuring parameter value of a faulty reference solder joint |
| PARiVALAVESJBREF | measuring parameter value derived from measuring parameter values of faulty reference solder joints |
| BOARD | substrate, circuit board |
| SM | solder material |
| PIN | contact element |
| CMP | component |
| CTA | contact area |
| CTAREF | contact area reference value |
| PAR | measuring parameter |
| 1, . . ., m | plurality of measuring parameters |
| 1, . . ., o | plurality of faulty reference solder joints |
| DFAi | fault actual-value range specific to a measuring parameter (parameter PARi) |
| UVDFAi | upper range limiting value of DFAi |
| LVDFAi | lower range limiting value of DFAi |
| Ti1 | first threshold value specific to a measuring parameter |
| Ti2 | second threshold value specific to a measuring parameter |
| a, b, c | threshold value deviation specific to a measuring parameter |
| ml | longitudinal extent of a solder joint (SJ, SJREF) |
| b | width extent of a solder joint (SJ, SJREF) |
| v | valley width of a cross section of a solder joint (SJ, SJREF) |
| hp | height difference between a vertex point (heel) and a valley point (pad) of a solder joint |
| phd | height difference between the valley point(pad) of the solder joint (SJ) and substrate (BOARD) |
| neg | fall in an edge region of a solder joint (SJ, SJREF) |
| sl | rise in an edge region of solder joint (SJ, SJREF) |
| d | quantity of material in a certain region of the solder joint (SJ, SJREF) |

What is claimed is:

1. A process for selecting at least one measuring parameter for testing a solder joint (SJ) for freedom from faults by means of X-rays, where the solder joint (SJ) is arranged on a substrate (BOARD), where a fault-free solder joint (SJG) has solder material (SM), where the solder material (SM) of said fault-free solder joint (SJG) is electrically connected to a contact element (PIN) of a component (CMP), and where the solder joint (SJ) is assigned to a predefinable solder-joint type as a function of a shape of the contact element (PIN) in the region of the solder joint (SJ), said process comprising the following steps:

before the solder joint (SJ) is tested, for each measuring parameter in a first number (m) of measuring parameters (PARi, i=1 . . . m) which characterize physical attributes of a solder joint, determining at least one of a lower range limiting value (LVDFAi) and an upper range limiting value (UVDFAi) of a fault actual-value range (DFAi) specific to a measuring parameter, a comparatively large fault in the solder joint (SJ) or a comparatively small fault in the solder joint (SJ) corresponding to the lower range limiting value (LVDFAi), a comparatively small fault in the solder joint (SJ) or a comparatively large fault in the solder joint (SJ) corresponding to the upper range limiting value (UVDFAi), the measuring parameters (PARi) in each case describing one of topography and internal structure of a second number (n) of fault-free reference solder joints (SJGREFj, j=1 . . . n), whereby at least one of m lower range limiting values (LVDFAi) and m upper range limiting values (UVDFAi) of fault actual-value ranges (DFAi) specific to a measuring parameter are determined;

before the solder joint (SJ) is tested, for each measuring parameter in the first number (m) of measuring parameters (PARi), ascertaining a measuring parameter value (PARiVALSJBREF) specific to a reference solder joint, for at least one faulty reference solder joint (SJBREF) of a type identical to the fault-free reference solder joint, so that at least m measuring parameter values (PARiVALSJBREF) specific to reference solder joints are ascertained for the m measuring parameters (PARi) for the at least one faulty reference solder joint (SJBREF);

before the solder joint (SJ) is tested, for each of the m measuring parameter values (PARiVALSJBREF), specific to a reference solder joint, of the faulty reference solder joints (SJBREF) determining its mathematical relationship, comprising one of a difference and a ratio, to one of the lower range limiting value (LVDFAi) and the upper range limiting value (UVDFAi) of the fault actual-value range (DFAi) specific to a measuring parameter;

during testing of a solder joint (SJ), identifying a measuring parameter value (PAR1VALSJ) of a first measuring parameter (PAR1) for which the measuring parameter value (PAR1VALSJBREF), specific to a reference solder joint, of the at least one faulty reference solder joint (SJBREF) is one of closest to and furthest from the lower range limiting value (LVDFA1) of the fault actual-value range (DFA1) specific to a measuring parameter, as compared with other fault actual-value ranges (DFA2, . . . , DFAm) specific to a measuring or for which the measuring parameter value (PAR1VALSJBREF), specific to a reference solder joint, of the at least one faulty reference solder joint (SJBREF) is one of furthest from and closest to the upper range limiting value (UVDFA1) of the fault actual-value range (DFA1) specific to a measuring parameter, as compared with fault actual-value ranges (DFA2, . . . , DFAm) specific to a measuring parameter.

2. The process according to claim 1, further comprising:
during testing of the solder joint (SJ), ascertaining at least one second measuring parameter value (PAR2VALSJ) of a second measuring parameter (PAR2) for which the measuring parameter value (PAR2VALSJBREF) specific to a reference solder joint of the at least one faulty reference solder joint (SJBREF) is one of second closest to and second furthest from the lower range limiting value (LVDFA2) of the fault actual-value range (DFA2) specific to a measuring parameter, as compared with fault actual-value ranges (DFA3, . . . , DFAm) for other measuring parameters, or for which the measuring parameter value (PAR2VALSJBREF) specific to a reference solder joint of the at least one faulty reference solder joint (SJBREF) is one of second furthest from and second closest to the upper range limiting value (UVDFA2) of the fault actual-value range (DFA2) specific to a measuring parameter, as compared with other fault actual-value ranges (DFA3, . . . , DFAm) specific to a measuring parameter.

3. The process according to claim 1, wherein:
before the solder joint (SJ) is tested, measuring parameter values (PARoVALSJBREF) of the first number (m) of measuring parameters (PARi) are ascertained for a third number (o) of faulty reference solder joints (SJBREFP, p=1 . . . o) of an identical type;

before the solder joint (SJ) is tested, at least one measuring parameter value (PARiVALAVESJBREF) of the faulty reference solder joints (SJBREF) is derived from the respective o measuring parameter values (PARoVALSJBREF), specific to a reference solder joint, of each measuring parameter (PARi) in accordance with a predefinable algorithm (AL1);

before the solder joint (SJ) is tested, instead of a mathematical relationship of the measuring parameter values (PARiVALSJBREF), for a reference solder joint of the faulty reference solder joints (SJBREF) of an identical type, to the lower range limiting value (LVDFAi) or the upper range limiting value (UVDFAi) of the respective fault actual-value range (DFAi) specific to a measuring parameter, a mathematical relationship of the derived measuring parameter values (PARiVALAVESJBREF), comprising one of a difference and a ratio, to the lower range limiting value (LVDFAi) or to the upper range limiting value (UVDFAi) of the respective fault actual-value range (DFAi) specific to a measuring parameter is determined; and during testing of the solder joint (SJ), instead of the measuring parameter value (PAR1VALSJ), a further measuring parameter value (PARi'VALSJ) of at least one further first measuring parameter (PARi') is ascertained, for which the derived measuring parameter value (PARiVALAVESJBREF) of the third number (o) of the faulty reference solder joints is one of closest to and furthest from the lower range limiting value (LVDFAi) of the fault actual-value range (DFAi), as compared with other fault actual-value ranges (DFA3, . . . DFAm) specific to a measuring parameter, or for which the derived measuring parameter value (PARiVALAVESJBREF) of the third number (o) of faulty reference solder joints one of furthest from and closest to the upper range limiting value (UVDFAi) of the fault actual-value range (DFAi), as compared with other fault actual-value ranges (DFA3, . . . , DFAm) specific to a measuring parameter.

4. The process according to claim 1, wherein one of the lower range limiting value (LVDFAi) and the upper range limiting value of the fault actual-value range (DFAi) specific to a measuring parameter is determined as a function of a measuring parameter value in which a faulty solder joint has an inadequate contact area between solder material and contact element (PIN).

5. The process according to claim 1, wherein one of the upper range limiting value (UVDFAi) and the lower range limiting value of the fault actual-value range (DFAi) for a measuring parameter is determined as a function of a distribution function of measuring parameter values (PARi) of the fault-free reference solder joints (SJREF).

6. The process according to claim 5, wherein:
the distribution function of measuring parameter values (PARi) of the fault-free reference solder joints is a normal distribution; and
one of the upper range limiting value (UVDFAi) and the lower range limiting value of the fault actual-value range (DFAi) specific to a measuring parameter is determined as a function of a standard deviation.

7. The process according to claim 1, wherein one of the upper range limiting value (UVDFAi) and the lower range limiting value of the fault actual-value range (DFAi) for a measuring parameter is fixed to a value which is slightly smaller or greater than the measuring parameter value of a still fault-free reference solder joint (SFGREF).

8. The process according to claim 1, wherein a solder joint (SJ) is judged to be fault-free during a testing if the measuring parameter value is one of at least as large and at most as small, as a predefinable, first threshold value (Ti1) for a measuring parameter.

9. The process according to claim 8, wherein the first threshold value (Ti1) for a measuring parameter is the same size as the upper range limiting value (UVDFAi) of the fault actual-value range (DFAi) for the measuring parameter.

10. The process according to claim 9, wherein a solder joint (SJ) is judged to be fault-free during testing if a measuring parameter value is at least as large as a predefinable, second threshold value (Ti2) specific to a measuring parameter, which threshold value differs, by a threshold value deviation (ia) specific to the measuring parameter, from the first threshold value (Ti1) specific to the measuring parameter.

11. The process according to claim 10, wherein one of the magnitude of a permissible threshold value deviation (a), specific to a measuring parameter, of a first measuring parameter, and the magnitudes of further permissible threshold value deviations (b, c), specific to a measuring parameter, of further measuring parameters is determined as a function of a predefinable reference value (CTAREF) of a mathematical combination of the threshold value deviations (a, b, c), comprising one of a product, an average and a sum of the threshold value deviations.

12. The process according to claim 10, wherein one of the magnitude of a permissible threshold value deviation (a), specific to a measuring parameter, of a first measuring parameter, and the magnitudes of further permissible threshold value deviations (b, c), specific to a measuring parameter, of further measuring parameters is determined as a function of a predefinable reference value (CTAREF) of a contact area (CTA) formed between the solder material (SM) and contact element (PIN) of a solder joint (SJ) to be tested.

13. The process according to claim 11, wherein
an item of information which designates the probability of the existence of an electrical contact between solder material (SM) and a contact element (PIN) is formed as a function of measuring parameter values of first measuring parameters; and
the magnitude of the contact area (CTA) is determined based on measuring parameter values of second measuring parameters.

14. The process according to claim 13, wherein the magnitude of the contact area (CTA) is determined based on an item of information which designates at least one of a longitudinal extent (ml) of the solder joint (SJ, SJREF), a width extent (b) of the solder joint (SJ), a valley width (v) of a cross section of the solder joint (SJ), a first height difference (hp) between a vertex point (heel) and a valley point (pad) of the solder joint, a second height difference (phd) between the valley point (pad) of the solder joint (SJ) and the substrate (BOARD), a fall (neg) in an edge region of the solder joint (SJ), a rise (sl) in an edge region of the solder joint (SJ), and a quantity of material (d) in a predefinable region of the solder joint (SJ).

15. The process according to claim 1, wherein process steps carried out before the solder joint (SJ) are tested, are carried out with a time offset.

16. The process according to claim 1, wherein:
a result of the test, one of a first item of information (INFSJG) and a second item of information (INFSJB) is formed;
the first item of information (INFSJG) indicates freedom from faults of a tested, fault-free solder joint (SJ), and the second item of information (INFSJB) indicates the presence of faults of a tested, faulty solder joint (SJ); and
the first or second item of information is used to control a process for producing solder joints.

17. The process according to claim 1 wherein:
said measuring parameters comprise gray-value measuring parameters; and
said measuring parameter values comprise gray-value measuring parameter values.

18. A process for testing a solder joint (SJ) for freedom from faults by means of X-rays,
where the solder joint (SJ) is arranged on a substrate (BOARD),
where solder material (SM) of a fault-free solder joint (SJ) is connected electrically to a contact element (PIN) of a component (CMP), and
where the solder joint (SJ) is assigned to a predefinable solder-joint type as a function of a shape of the contact element (PIN) in the region of the solder joint (SJ),
said process comprising:
testing the solder joint (SJ) to determine a magnitude of a contact area (CTA) formed between the solder material (SM) and contact element (PIN);
comparing the magnitude of the contact area (CTA) formed between the solder material (SM) and contact element (PIN) with a predefinable contact-area reference value (CTAREF); and
judging the solder joint (SJ) to be fault-free solder joint (SJG) or a faulty solder joint (SJB) as a function of a result of the comparison.

19. The process according to claim 18, wherein said testing step comprises:
generating an item of information which designates a probability of the existence of an electrical contact between the solder material (SM) and contact element (PIN) as a function of measuring parameter values of first measuring parameters (PM1); and
determining the magnitude of the contact area (CTA) as a function of measuring parameter values of second measuring parameters (PM2).

20. The process according to claim 19, wherein:
the first measuring parameter is a measuring parameter that designates at least one of a meniscus of a solder joint and solder material (SM) arranged laterally on the contact element (PIN); and
the second measuring parameter designates at least one of a longitudinal extent (ml) of the solder joint (SJ, SJREF), a width extent (b) of the solder joint (SJ), a valley width (v) of a cross section of the solder joint (SJ), a first height difference (hp) between a vertex point (heel) and a valley point (pad) of the solder joint, a second height difference (phd) between the valley point (pad) of the solder joint (SJ) and the substrate (BOARD), a fall (neg) in an edge region of the solder joint (SJ), a rise (sl) in an edge region of the solder joint (SJ), and a quantity of material (d) in a predefinable region of the solder joint (SJ).

21. A circuit arrangement (SJTD) for selecting at least one measuring parameter for a solder joint (SJ) for freedom from faults by means of X-rays, wherein:

the circuit arrangement has a data processing device (C) with an associated control program;

the solder joint (SJ) is arranged on a substrate (BOARD);

a fault-free solder joint (SJG) has solder material (SM);

the solder material (SM) of a fault-free solder joint (SJG) is connected electrically to a contact element (PIN) of a component (CMP);

the solder joint (SJ) is assigned to a predefinable solder-joint type as a function of a shape of the contact element (PIN) in a region of the solder joint (SJ); and the control program embodies the Process according to one of the preceding claims.

22. The circuit arrangement according to claim 20, wherein the control program is further configured such that:

during testing of the solder joint (SJ), ascertaining at least one second measuring parameter value (PAR2VALSJ) of a second measuring parameter (PAR2) for which the measuring parameter value (PAR2VALSJBREF) specific to a reference solder joint of the at least one faulty reference solder joint (SJBREF) is one of second closest to and second furthest from the lower range limiting value (LVDFA2) of the fault actual-value range (DFA2) specific to a measuring parameter, as compared with other fault actual-value ranges (DFA3, . . . , DFAm) specific to a measuring parameters, or for which the measuring parameter value (PAR2VALSJBREF) specific to a reference solder joint of the at least one faulty reference solder joint (SJBREF) is one of second furthest from and second closest to the upper range limiting value (UVDFA2) of the fault actual-value range (DFA2) specific to a measuring parameter, as compared with other fault actual-value ranges (DFA3, . . . , DFAm) specific to a measuring parameter.

23. The circuit arrangement according to claim 20, wherein the control program is configured such that:

before the solder joint (SJ) is tested, measuring parameter values (PARoVALSJBREF) of the first number (m) of measuring parameters (PARi) are ascertained for a third number (o) of faulty reference solder joints (SJBREFP, p=1 . . . o) of an identical type;

before the solder joint (SJ) is tested, at least one measuring parameter value (PARiVALAVESJBREF) of the faulty reference solder joints (SJBREF) is derived from the respective o measuring parameter values (PARoVALSJBREF), specific to a reference solder joint, of each measuring parameter (PARi) in accordance with a predefinable algorithm (AL1);

before the solder joint (SJ) is tested, instead of a mathematical relationship of the measuring parameter values (PARiVALSJBREF), for a reference solder joint of the faulty reference solder joints (SJBREF) of an identical type, to the lower range limiting value (LVDFAi) or the upper range limiting value (UVDFAi) of the respective fault actual-value range (DFAi) specific to a measuring parameter, a mathematical relationship of the derived measuring parameter values (PARiVALAVESJBREF), comprising one of a difference and a ratio, to the lower range limiting value (LVDFAI) or to the upper range limiting value (UVDFAi) of the respective fault actual-value range (DFAi) specific to a measuring parameter is determined; and during testing of the solder joint (SJ), instead of the measuring parameter value (PAR1VALSJ), a further measuring parameter value (PARi'VALSJ) of at least one further first measuring parameter (PARi') is ascertained, for which the derived measuring parameter value (PARiVALAVESJBREF) of the third number (o) of the faulty reference solder joints is one of closest to and furthest from the lower range limiting value (LVDFAi) of the fault actual-value range (DFAi), as compared with other fault actual-value ranges (DFA3, . . . DFAm) specific to a measuring parameter, or for which the derived measuring parameter value (PARiVALAVESJBREF) of the third number (o) of faulty reference solder joints one of furthest from and closest to the upper range limiting value (UVDFAi) of the fault actual-value range (DFAi), as compared with other fault actual-value ranges (DFA3, . . . , DFAm) specific to a measuring parameter.

24. The circuit arrangement according to claim 20, wherein the control program is configured such that one the lower range limiting value (LVDFAi) and the upper range limiting value of the fault actual-value range (DFAi) specific to a measuring parameter is determined as a function of a measuring parameter value in which a faulty solder joint has an inadequate contact area between solder material and contact element (PIN).

25. The circuit arrangement according to claim 20, wherein the control program is configured such that one of the upper range limiting value (UVDFAi) and the lower range limiting value of the fault actual-value range (DFAi) for a measuring parameter is determined as a function of a distribution function of measuring parameter values (PARi) of the fault-free reference solder joints (SJREF).

26. The circuit arrangement according to claim 20, wherein the control program is configured such that:

the distribution function of measuring parameter values (PARi) of the fault-free reference solder joints is a normal distribution; and one of the upper range limiting value (UVDFAi) and the lower range limiting value of the fault actual-value range (DFAi) specific to a measuring parameter is determined as a function of a standard deviation.

27. The circuit arrangement according to claim 20, wherein the control program is configured such that one of the upper range limiting value (UVDFAi) and the lower range limiting value of the fault actual-value range (DFAi) for a measuring parameter is fixed to a value which is slightly smaller or greater than the measuring parameter value of a still fault-free reference solder joint (SFGREF).

28. The circuit arrangement according to claim 20, wherein the control program is configured such that a solder joint (SJ) is judged to be fault-free during testing if the measuring parameter value is one of at least as large and at most as small as a predefinable, first threshold value (Ti1) for a measuring parameter.

29. The circuit arrangement according to claim 28, wherein the control program is configured such that the first threshold value (Ti1) for a measuring parameter is of the same size as the upper range limiting value (UVDFAi) of the fault actual-value range (DFAi) for the measuring parameter.

30. The circuit arrangement according to claim 29, wherein the control program is configured such that a solder joint (SJ) is judged to be fault-free during the testing if a measuring parameter value is at least as large as a predefinable, second threshold value (Ti2) specific to a measuring parameter, which threshold value differs, by a threshold value deviation (ia) specific to the measuring parameter, from the first threshold value (Ti1) specific to the measuring parameter.

31. The circuit arrangement according to claim 30, wherein the control program is configured such that one of the magnitude of a permissible threshold value deviation (a), specific to a measuring parameter, of a first measuring parameter, and the magnitudes of further permissible threshold value deviations (b, c), specific to a measuring parameter, of further measuring parameters is determined as a function of a predefinable reference value (CTAREF) of a mathematical combination of the threshold value deviations (a, b, c), comprising one of a product, an average and a sum of the threshold value deviations.

32. The circuit arrangement according to claim 30, wherein the control program is configured such that one of the magnitude of a permissible threshold value deviation (a), specific to a measuring parameter, of a first measuring parameter, and the magnitudes of further permissible threshold value deviations (b, c), specific to a measuring parameter, of further measuring parameters is determined as a function of a predefinable reference value (CTAREF) of a contact area (CTA) formed between the solder material (SM) and contact element (PIN) of a solder joint (SJ) to be tested.

33. The circuit arrangement according to claim 32, wherein the control program is configured such that:
  an item of information which designates the probability of the existence of an electrical contact between solder material (SM) and a contact element (PIN) is formed as a function of measuring parameter values of first measuring parameters; and
  the magnitude of the contact area (CTA) is determined based on measuring parameter values of second measuring parameters.

34. The circuit arrangement according to claim 33, wherein the control program is configured such that the magnitude of the contact area (CTA) is determined based on an item of information which designates at least one of a longitudinal extent (ml) of the solder joint (SJ, SJREF), a width extent (b) of the solder joint (SJ), a valley width (v) of a cross section of the solder joint (SJ), a first height difference (hp) between a vertex point (heel) and a valley point (pad) of the solder joint, a second height difference (phd) between the valley point (pad) of the solder joint (SJ) and the substrate (BOARD), a fall (neg) in an edge region of the solder joint (SJ), a rise (sl) in an edge region of the solder joint (SJ), and a quantity of material (d) in a predefinable region of the solder joint (SJ).

35. The circuit arrangement according to claim 21, wherein the control program is configured such that process steps carried out before the solder joint (SJ) is tested are carried out with a time offset.

36. The circuit arrangement according to claim 21, wherein the control program is configured such that:
  as a result of the test, one of a first item of information (INFSJG) and a second item of information is formed;
  the first item of information (INFSJG) indicates freedom from faults of a tested, fault-free solder joint (SJ), and the second item of information (INFSJB) indicates the presence of faults of a tested, faulty solder joint (SJ); and
  the first or second item of information is used to control a process for producing solder joints.

37. The circuit arrangement according to claim 21, wherein the control program is configured to perform the following steps:
  before the solder joint (SJ) is tested, for each measuring parameter in a first number (m) of measuring parameters (PARi, i=1 . . . m) which characterize physical attributes of a solder joint, determining at least one of a lower range limiting value (LVDFAi) and an upper range limiting value (UVDFAi) of a fault actual-value range (DFAi) specific to a measuring parameter, a comparatively large fault in the solder joint (SJ) or a comparatively small fault in the solder joint (SJ) corresponding to the lower range limiting value (LVDFAi), a comparatively small fault in the solder joint (SJ) or a comparatively large fault in the solder joint (SJ) corresponding to the upper range limiting value (UVDFAi), the measuring parameters (PARi) in each case describing one of topography and internal structure of a second number (n) of fault-free reference solder joints (SJGREFj, j=1 . . . n), whereby at least one of m lower range limiting values (LVDFAi) and m upper range limiting values (UVDFAi) of fault actual-value ranges (DFAi) specific to a measuring parameter are determined;
  before the solder joint (SJ) is tested, for each measuring parameter the first number (m) of measuring parameters (PARi), ascertaining a measuring parameter value (PARiVALSJBREF) specific to a reference solder joint, for at least one faulty reference solder joint (SJBREF) of a type identical to the fault-free reference solder joint, so that at least m measuring parameter values (PARiVALSJBREF) specific to reference solder joints are ascertained for the m measuring parameters (PARi) for the at least one faulty reference solder joint (SJBREF);
  before the solder joint (SJ) is tested, for each of the m measuring parameter values (PARiVALSJBREF), specific to a reference solder joint, of the faulty reference solder joints (SJBREF) determining its mathematical relationship, comprising one of a difference and a ratio, to one of the lower range limiting value (LVDFAi) and the upper range limiting value (UVDFAi) of the fault actual-value range (DFAi) for a measuring parameter;
  during testing of solder joint (SJ), identifying a measuring parameter value (PAR1VALSJ) of a first measuring parameter (PAR1) for which the measuring parameter value (PAR1VALSJBREF), specific to a reference solder joint, of the at least one faulty reference solder joint (SJBREF) is one of closest to and furthest from the lower range limiting value (LVDFA1) of the fault actual-value range (DFA1) specific to a measuring parameter, as compared with other fault actual-value ranges (DFA2, . . . , DFAm) specific to a measuring parameter, or for which the measuring parameter value (PAR1VALSJBREF), specific to a reference solder joint, of the at least one faulty reference solder joint (SJBREF) is one of furthest from and closest to the upper range limiting value (UVDFA1) of the fault actual-value range (DFA1) specific to a measuring parameter, as compared with other fault actual-value ranges (DFA2, . . . , DFAm) specific to a measuring parameter.

38. The process according to claim 21 wherein:

said measuring parameters comprise gray-value measuring parameters; and said measuring parameter values comprise gray-value measuring parameter values.

39. A circuit arrangement of testing a solder joint (SJ) for freedom from faults by means of X-rays, wherein:

the solder joint (SJ) is arranged on a substrate (BOARD), solder material (SM) of a fault-free solder joint (SJ) is connected electrically to a contact element (PIN) of a component (CMP), and the solder joint (SJ) is assigned to a predefinable solder-joint type as a function of a shape of the contact element (PIN) in the region of the solder joint (SJ), the circuit arrangement includes a processor for performing a control program that is configured such that the solder joint (SJ) is tested to determine a magnitude of a contact area (CTA) formed between the solder material (SM) and contact element (PIN);

the magnitude of the contact area (CTA) formed between the solder material (SM) and contact element (PIN) is compared with a predefinable contact-area reference value (CTAREF); and the solder joint (SJ) is judged to be a fault-free solder joint (SJG) or to be a faulty solder joint (SJB) as a function of a result of the comparison.

40. The circuit arrangement according to claim 39, wherein the control program is configured such that:

an item of information which designates a probability of the existence of an electrical contact between the solder material (SM) and contact element (PIN) is generated as a function of measuring parameter values of first measuring parameters (PM1); and the magnitude of the contact area (CTA) is determined as a function of measuring parameter values of second measuring parameters (PM2).

41. The circuit arrangement according to claim 40, wherein the control program is configured such that:

the first measuring parameter is a measuring parameter which designates at least one of a meniscus of a solder joint and solder material (SM) arranged laterally on the contact element (PIN); and the second measuring parameter designates at least one of a longitudinal extent (ml) of the solder joint (SJ, SJREF), a width extent (b) of the solder joint (SJ), a valley width (v) of a cross section of the solder joint (SJ), a first height difference (hp) between a vertex point (heel) and a valley point (pad) of the solder joint, a second height difference (phd) between the valley point (pad) of the solder joint (SJ) and the substrate (BOARD), a fall (neg) in an edge region of the solder joint (SJ), a rise (sl) in an edge region of the solder joint (SJ), and a quantity of material (d) in a predefinable region of the solder joint (SJ).

* * * * *